United States Patent
Schmidt-Weber et al.

(10) Patent No.: US 11,821,894 B2
(45) Date of Patent: Nov. 21, 2023

(54) RATIO OF IMMUNE CELLS AS PROGNOSTIC INDICATOR OF THERAPEUTIC SUCCESS IN ALLERGEN-SPECIFIC IMMUNOTHERAPY

(71) Applicant: KLINIKUM RECHTS DER ISAR DER TECHNISCHEN UNIVERSITÄT MÜNCHEN, Munich (DE)

(72) Inventors: Carsten B. Schmidt-Weber, Munich (DE); Adam M. Chaker, Munich (DE); Ulrich M. Zissler, Truchtlaching (DE); Constanze A. Jakwerth, Munich (DE)

(73) Assignee: KLINIKUM RECHTS DER ISAR DER TECHNISCHEN UNIVERSITÄT MÜNCHEN, Munich (DE)

( * ) Notice: Subject to any disclaimer, the term of this patent is extended or adjusted under 35 U.S.C. 154(b) by 697 days.

(21) Appl. No.: 16/625,503

(22) PCT Filed: Jun. 21, 2018

(86) PCT No.: PCT/EP2018/066648
§ 371 (c)(1),
(2) Date: Dec. 20, 2019

(87) PCT Pub. No.: WO2018/234493
PCT Pub. Date: Dec. 27, 2018

(65) Prior Publication Data
US 2021/0333264 A1    Oct. 28, 2021

(30) Foreign Application Priority Data

Jun. 23, 2017 (EP) .................... 17177681

(51) Int. Cl.
*G01N 33/50* (2006.01)
*G01N 33/68* (2006.01)

(52) U.S. Cl.
CPC ....... *G01N 33/505* (2013.01); *G01N 33/6869* (2013.01); *G01N 2800/24* (2013.01); *G01N 2800/52* (2013.01)

(58) Field of Classification Search
CPC ............ G01N 33/505; G01N 33/6869; G01N 2800/24; G01N 2800/52
See application file for complete search history.

(56) References Cited

FOREIGN PATENT DOCUMENTS

WO    2016079363 A1    5/2016

OTHER PUBLICATIONS

Pfaar (Int Arch Allergy Imunol 2013 160:420-424) (Year: 2013).*
Demoly (Clin Transl Allergy 2015 5:18). (Year: 2015).*
Amar (J. Allergy Clin Immunol 2009 124:150-6). (Year: 2009).*
DuBuske (Allergy Asthma Proc 2011 32:239-247). (Year: 2011).*
Feng (PLOS One 2014 9:e86529). (Year: 2014).*
Braza, F. et al., "A regulatory CD9+ B-cell subset inhibits HDM-induced allergic airway inflammation," Allergy, vol. 70, No. 11, pp. 1421-1431, Aug. 2015.
Pang, Nannan et al. "Increased IL-10/IL-17 ratio is aggravated along with the prognosis of patients with chronic lymphocytic leukemia," International Immunopharmacology, vol. 40, pp. 57-64, :57-64, Nov. 1, 2016.
Zissler, U. et al., Munich: "DZL Annual Meeting 2017", DZL Annual Meeting, Jan. 1, 2017, Abstract No. 71, entitled "Regulatory B cells and Shift in Th17 cell populations raise in Allergen-specific Immunotherapy".

* cited by examiner

*Primary Examiner* — Changhwa J Cheu
(74) *Attorney, Agent, or Firm* — SALIWANCHIK, LLOYD & EISENSCHENK

(57) ABSTRACT

The present invention relates to a ratio of immune cells for use in a method of predicting therapeutic success of an allergen-specific immunotherapy (AIT) in a patient suffering from or having a disposition to develop an allergic disease. Furthermore, the present invention also relates to a kit for predicting therapeutic success of an allergen-specific immunotherapy in a patient suffering from or having a disposition to develop an allergic disease. Furthermore, the present invention relates to a method of predicting therapeutic success of an allergen-specific immunotherapy (AIT) in a patient suffering from or having a disposition to develop an allergic disease.

15 Claims, 10 Drawing Sheets

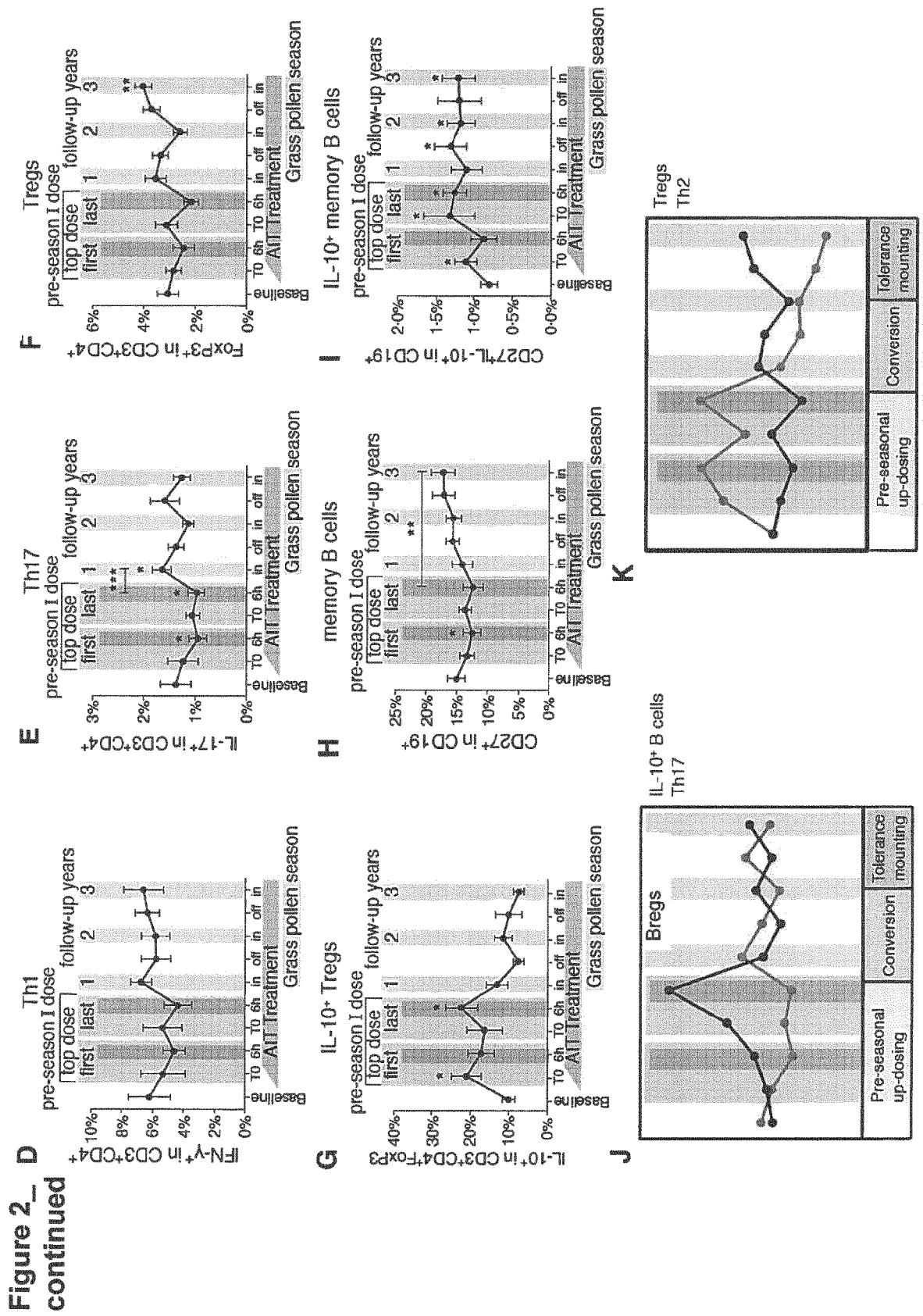

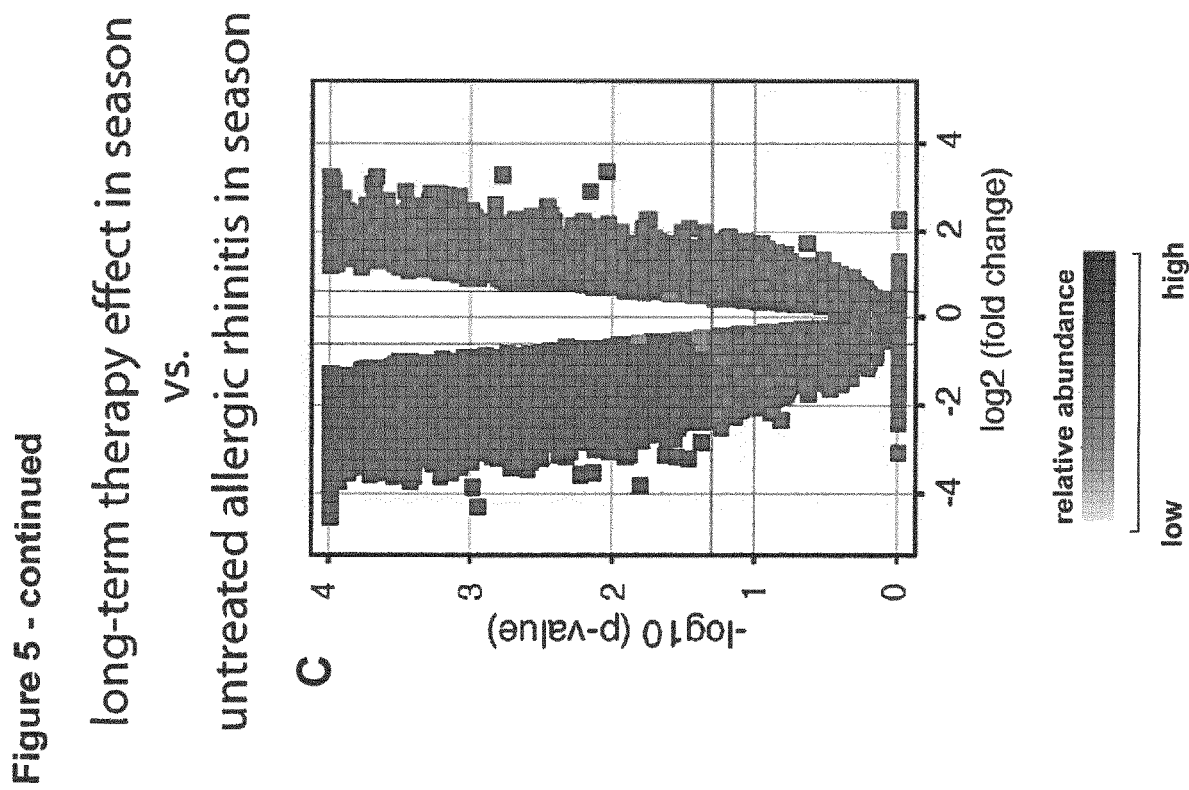
Figure 5 - continued

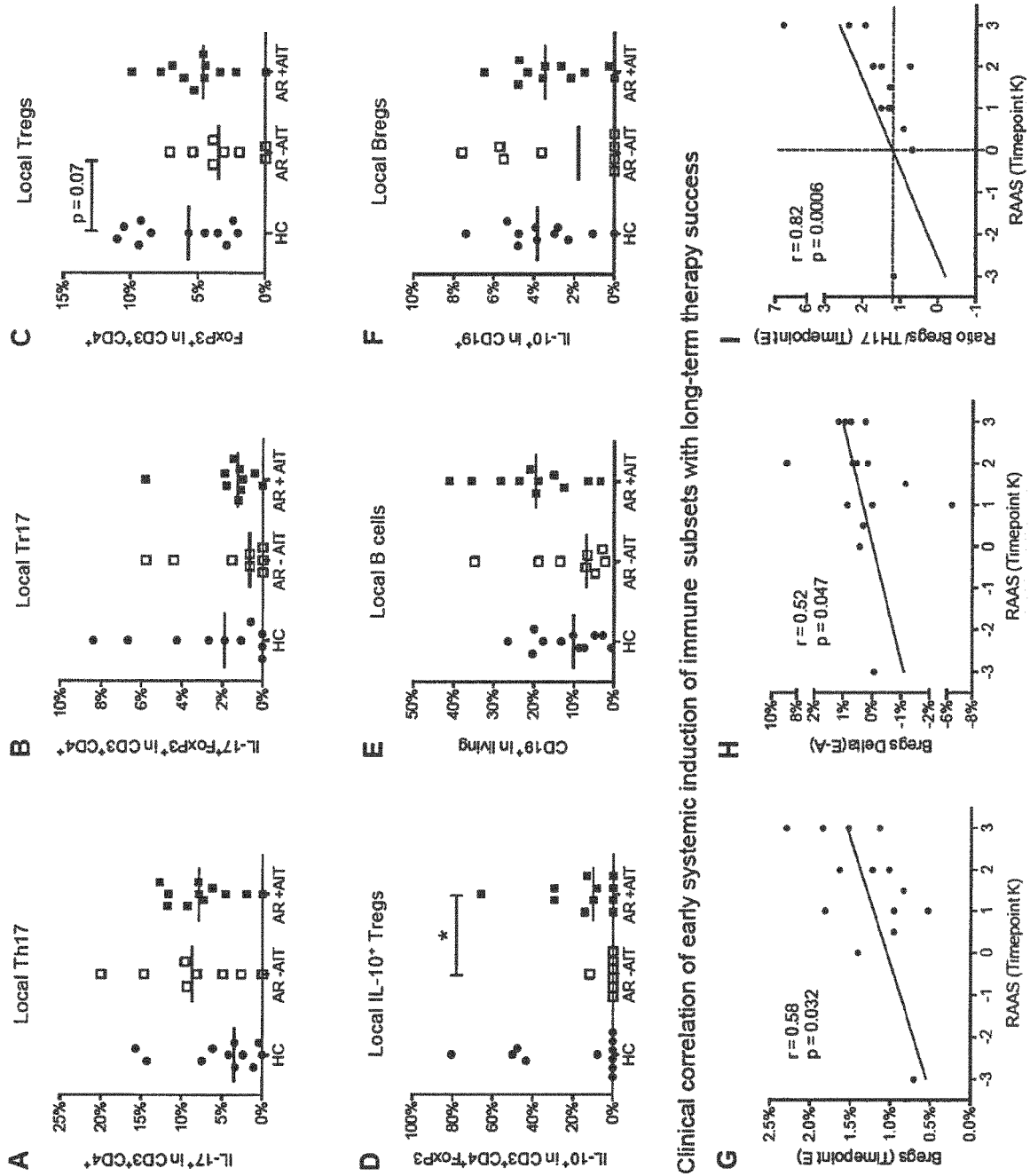

RATIO OF IMMUNE CELLS AS PROGNOSTIC INDICATOR OF THERAPEUTIC SUCCESS IN ALLERGEN-SPECIFIC IMMUNOTHERAPY

CROSS REFERENCE TO RELATED APPLICATIONS

This application is a National Stage Application of International Application Number PCT/EP2018/066648, filed Jun. 21, 2018; which claims priority to European Patent Application Number 17 177 681.8, filed Jun. 23, 2017.

FIELD OF THE INVENTION

The present invention relates to a ratio of immune cells for use in a method of predicting therapeutic success of an allergen-specific immunotherapy (AIT) in a patient suffering from or having a disposition to develop an allergic disease. Furthermore, the present invention also relates to a kit for predicting therapeutic success of an allergen-specific immunotherapy in a patient suffering from or having a disposition to develop an allergic disease. Furthermore, the present invention relates to a method of predicting therapeutic success of an allergen-specific immunotherapy (AIT) in a patient suffering from or having a disposition to develop an allergic disease.

BACKGROUND OF INVENTION

For patients with allergic diseases, such as allergic rhinitis and allergic asthma, there are different ways of treatment available: These patients can try to prevent exposure to the respective allergen altogether which, however, is severely limited in that such exposure cannot always be avoided without severe impairment of quality of life. Secondly, there is a wide range of therapeutic treatments available, mainly based on treatment with antihistamines and/or glucocorticoids. Such a therapy is frequently accompanied with side effects and has a tendency to lose efficacy over time. Moreover, long-term intake of medication may lead to cumulated adverse-effects especially in the case of steroids and importantly: symptomatic medication does not change the course of disease. In contrast thereto and as a third possibility, patients, prior to exposure to the seasonally related allergens may undergo a desensitization or hyposensitization allergen-treatment such that they get artificial exposure to defined doses of allergen and thereby hopefully become less sensitive to it. This latter therapy is also sometimes referred to as allergen-specific immunotherapy (AIT) and involves the artificial and repeated exposure to defined doses of allergen, for example by subcutaneous application with a syringe or in a sublingual manner. Such allergen-specific immunotherapy typically is prolonged over several years and may not be effective or suitable for every patient treated therewith. For this reason, there is a need in the art to be able to determine and predict an individual patient's therapeutic response to an allergen-specific immunotherapy or the effectiveness of an allergen-specific immunotherapy towards an individual patient. Being able to predict, at an early stage of such treatment, whether or not it is at all useful to conduct such an allergen-specific immunotherapy would be of great benefit for the respective patient.

BRIEF SUMMARY

Accordingly, it was an object of the present invention to be able to predict therapeutic success of an allergen-specific immunotherapy in a patient.

This object is solved by a ratio of gene expression signatures or cell counts of interleukin-10 producing regulatory B-cells (IL-10$^+$ Bregs) and interleukin-17 producing T-helper cells (Th17), said ratio being designated as "IL-10$^+$Bregs/Th17", for use in a method of predicting therapeutic success of an allergen-specific immunotherapy (AIT) in a patient suffering from or having a disposition to develop an allergic disease selected from hay fever, allergic rhinitis, allergic asthma, allergic conjunctivitis, food allergy and stinging insect hypersensitivity.

This object is also solved by a method of predicting therapeutic success of an allergen-specific immunotherapy (AIT) in a patient suffering from or having a disposition to develop an allergic disease selected from hay fever, allergic rhinitis, allergic asthma, allergic conjunctivitis, food allergy and stinging insect hypersensitivity, wherein said method comprises the steps:

determining a ratio of interleukin-10 producing regulatory B-cells (IL-10$^+$ Bregs) and interleukin-17 producing T-helper cells (Th17) of said patient, said ratio being represented by IL-10$^+$Bregs/Th17, predicting therapeutic success of an allergen-specific immunotherapy in patient, if said determined ratio exceeds a defined threshold.

BRIEF DESCRIPTION OF THE FIGURES

The invention is now further described by reference to the figures, wherein.

DETAILED DESCRIPTION

Figure 1:
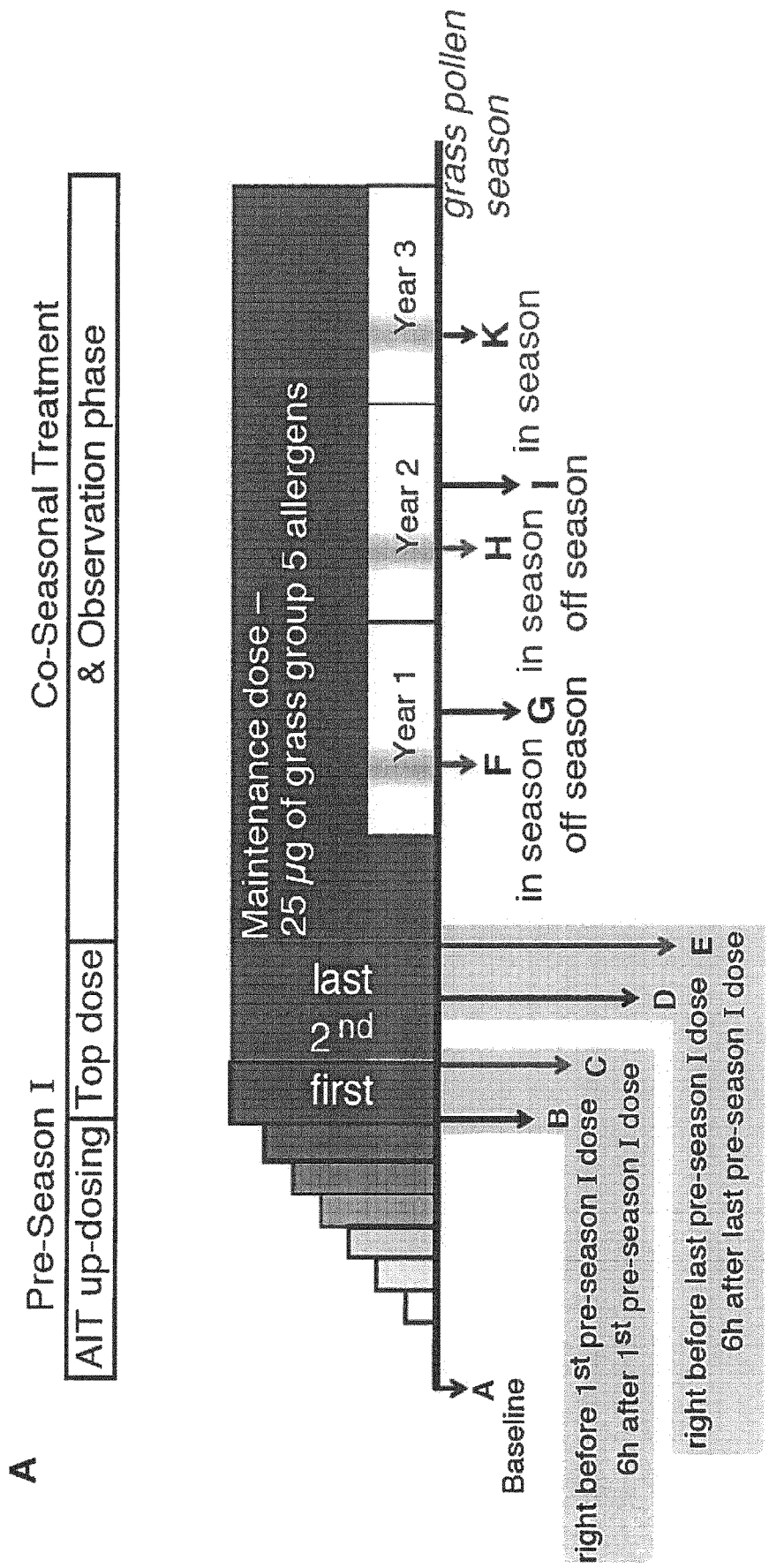
FIG. 1 shows that an increase of regulatory B-cells following an initial allergen-specific immunotherapy (AIT) coincides with a reduction of Th1 and Th17 cell counts during pre-seasonal up-dosing in year 1 of an allergen-specific immunotherapy.
Figure 1:
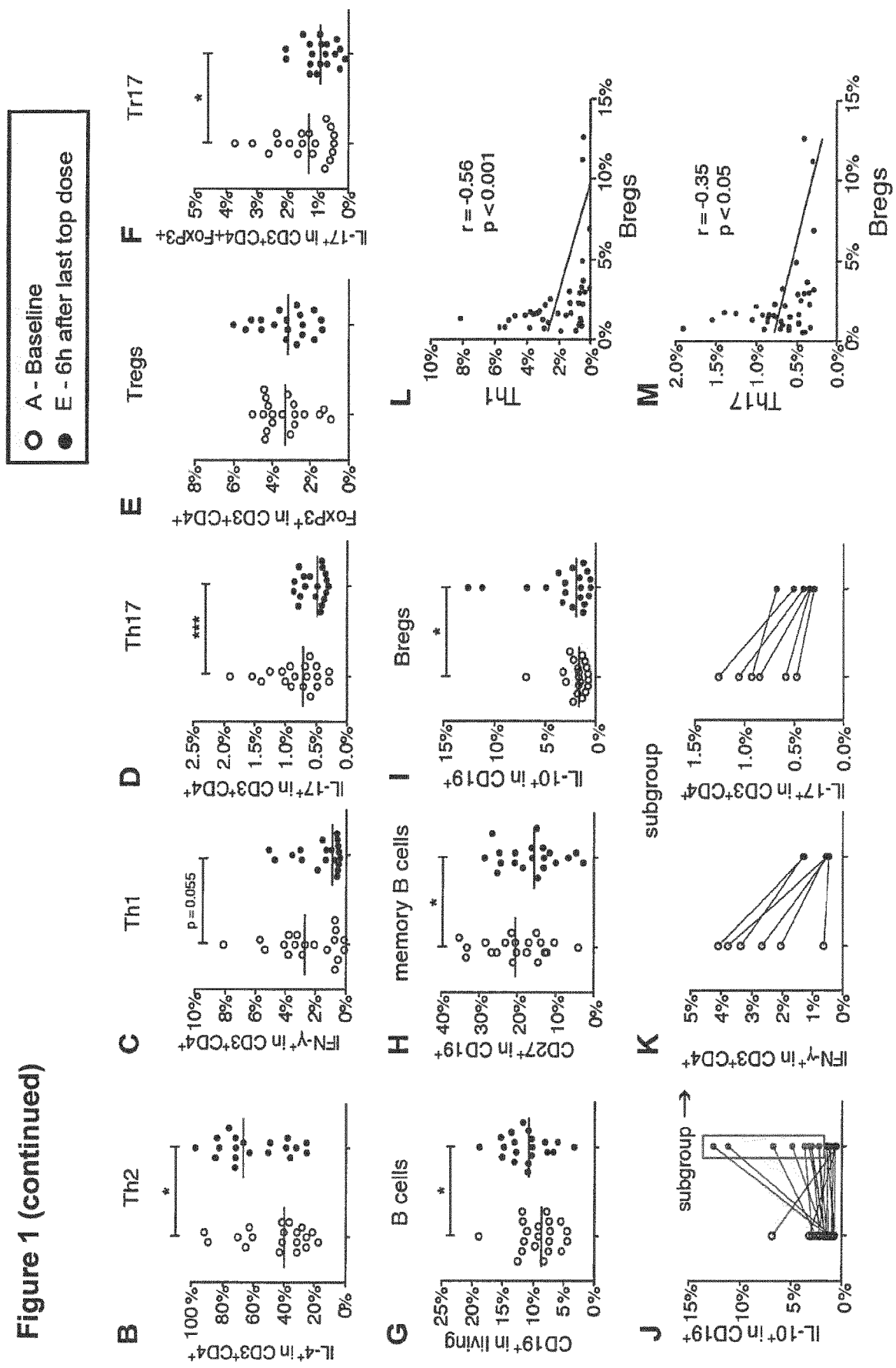

In one embodiment, said allergen-specific immunotherapy comprises an initial induction phase, wherein an allergen is repeatedly administered to a patient in increasing doses of said allergen up to a maximum dose effective to induce immunologic tolerance to said allergen in said patient, and a maintenance phase, wherein said allergen is administered repeatedly to said patient at said maximum dose, and wherein, in said method, said ratio is determined in the first 1-7 weeks of the maintenance phase after the initial induction phase.

In one embodiment, said allergen-specific immunotherapy involves subcutaneous injection of an allergen and comprises an initial induction phase, where said allergen is repeatedly, preferably weekly, subcutaneously administered to a patient in increasing doses of said allergen up to a maximum dose effective to induce immunologic tolerance to said allergen in said patient, and a maintenance phase, wherein said allergen is subcutaneously administered repeatedly to said patient at said maximum dose, wherein, preferably, said maintenance phase comprises a first subphase ("top dose phase") wherein said allergen is subcutaneously administered repeatedly at said maximum dose in a weekly or biweekly interval, and a second subphase ("treatment maintenance phase"), wherein said allergen is subcutaneously administered repeatedly at the same maximum dose in intervals longer than during the top-dose phase, preferably every 4-6 weeks, wherein said ratio is determined 4-10 hours after administration of any maximum dose of said top-dose phase, preferably 4-10 hours after administration of the last maximum dose of said top-dose phase.

Such allergen-specific immunotherapy involving the subcutaneous administration of allergen to a patient is also sometimes referred to as "subcutaneous allergen immunotherapy" or "subcutaneous immunotherapy" or "SCIT".

In another embodiment, said allergen-specific immunotherapy involves sublingual administration of an allergen and comprises an initial induction phase, where said allergen is repeatedly, preferably every other day, sublingually administered to a patient in increasing doses of said allergen up to a maximum dose effective to induce immunologic tolerance to said allergen in said patient, and a maintenance phase, wherein said allergen is repeatedly, preferably daily, sublingually administered to said patient at said maximum dose, wherein said ratio is determined within the first 1-7 weeks of said maintenance phase, preferably 4-10 hours after administration of any maximum dose of said maintenance phase within said first 1-7 weeks of said maintenance phase.

Such allergen-specific immunotherapy involving the sublingual administration of allergen to a patient is also sometimes referred to as "sublingual allergen immunotherapy" or "sublingual immunotherapy" or "SLIT".

In one embodiment, said ratio of cell counts of interleukin-10 producing regulatory B-cells (IL-10$^+$ Bregs) and interleukin-17 producing T-helper cells (Th17) of said patient is determined in one or several samples obtained from said patient, said sample(s) being selected from whole blood, peripheral blood mononuclear cells (PBMCs), nasal cells obtained from nasal scrapings or a nasal biopsy of said patient, bronchial cells obtained from sputum, a lung biopsy or bronchial alveolar lavage fluid (BALF) of said patient.

In one embodiment, therapeutic success is measured by a patient-assessed retrospective assessment of seasonal allergic symptoms (RAAS), or by combined symptom medication score (CSMS) or by visual analog score (VAS).

In one embodiment, said ratio IL-10$^+$ Bregs/Th17 is a ratio of gene expression signatures of IL-10$^+$ Bregs versus gene expression signatures of Th17 and is determined by determining gene expression signatures of IL-10$^+$ Bregs versus gene expression signatures of Th17 cells, wherein preferably said gene expression signatures are determined by a method selected from transcriptome-based assays, real time PCR and protein detection methods.

In one embodiment, said ratio of interleukin-10 producing regulatory B-cells (IL-10$^+$ Bregs) and interleukin-17 producing T-helper cells (Th17), represented by IL-10$^+$ Bregs/Th17, is a ratio of cell counts of these cells.

In one embodiment, said step of predicting comprises predicting therapeutic success of an allergen-specific immunotherapy in said patient, if said determined ratio of cell counts has a value in the range of ≥1.2, or comprises predicting no therapeutic success if said determined ratio of cell counts has a value in the range <1.2.

In one embodiment, said method of predicting therapeutic success comprises determining said ratio of cell counts, IL-10$^+$ Bregs/Th17, and said ratio of cell counts is determined by determining relative cell counts for both IL-10$^+$ Bregs and Th17 cells and by subsequently calculating the ratio of these relative cell counts, wherein said relative cell count of IL-10$^+$ Bregs cells is determined as number of IL-10$^+$ Bregs with reference to the number of live CD19$^+$ B-cells, and wherein said relative cell count of Th17 cells is determined as number of Th17 cells with reference to the number of live CD4$^+$ CD3$^+$ T-cells.

In one embodiment, said cell counts of "IL-10$^+$ Bregs" and of "Th17 cells" are determined by a method selected from flow cytometry, fluorescence-activated cell sorting (FACS), determining cell counts by means of a Coulter counter, a haemo-cytometer, image analysis or spectrophotometry.

In one embodiment, said method of predicting therapeutic success of an allergen-specific immunotherapy is an in-vitro method. In one embodiment, said method of predicting therapeutic success of an allergen-specific immunotherapy is an ex-vivo method.

In one embodiment, said allergic disease is selected from allergic rhinitis, hay fever and allergic asthma, and in such embodiment, said allergen is selected from pollen, in particular grass pollen, tree pollen and weed pollen, other airborne allergens, such as fungi, fungal spores, dust, mites, and animal dander.

The objects of the present invention are also solved by kit for predicting therapeutic success of an allergen-specific immunotherapy (AIT) in a patient suffering from or having a disposition to develop an allergic disease selected from hay fever, allergic rhinitis, allergic asthma, allergic conjunctivitis, food allergy and stinging insect hypersensitivity, in particular a kit for performing a method according to the present invention, as defined herein, said kit comprising:

Means to obtain a sample from said patient suffering from or having a disposition to develop an allergic disease, said sample being selected from whole blood, peripheral blood mononuclear cells (PBMCs), nasal cells obtained from nasal scrapings or a nasal biopsy of said patient, bronchial cells obtained from sputum, a lung biopsy or bronchial alveolar lavage fluid (BALF) of said patient;

means to perform a quantitative determination of gene expression signatures or cell counts of interleukin-10 producing regulatory B-cells (IL-10$^+$ Bregs) and interleukin-17 producing T-helper cells (Th17) in said sample, wherein said cell counts of IL-10$^+$ Bregs and Th17 are relative cell counts, wherein said relative cell count of IL-10$^+$ Bregs cells is determined as number of IL-10$^+$ Bregs with reference to the number of live CD19$^+$ B-cells, and wherein said relative cell count of Th17 cells is determined as number of Th17 cells with reference to the number of live CD4$^+$ CD3$^+$ T-cells.

In one embodiment, said kit further comprises:

Means to determine a ratio of gene expression signatures or cell counts of IL-10$^+$ Bregs and Th17, namely IL-10$^+$ Bregs/Th17.

In one embodiment, the kit according to the present invention, further comprises:

A set of instructions for use of said kit, said instructions indicating a threshold, wherein, if a determined ratio is ≥ said threshold, such ratio indicates therapeutic success of an allergen-specific immunotherapy, and if a determined ratio is < said threshold, such ratio indicates no therapeutic success of an allergen-specific immunotherapy.

In one embodiment of said kit, said ratio is a ratio of cell counts and said threshold is 1.2.

The present inventors have surprisingly found that the ratio of gene expression signatures or cell counts of interleukin-10 producing regulatory B-cells (IL-10$^+$ Bregs) and of interleukin-17 producing T-helper cells (Th17), that is IL-10$^+$ Bregs/Th17, is a good prognostic indicator for predicting therapeutic success of an allergen-specific immunotherapy (AIT) in a patient who suffers from or has a disposition to develop an allergic disease, such as hay fever, allergic rhinitis, allergic asthma, allergic conjunctivitis, food allergy or stinging insect hypersensitivity. Such parameter can be determined at an early stage of the allergen-specific immunotherapy and can thus be used to decide whether or not to continue with the allergen-specific immunotherapy. The present inventors have surprisingly found that if such ratio of cell counts is equal or above a threshold value of 1.2, it is highly likely that the allergen-specific immunotherapy (AIT) will be therapeutically successful. In one embodiment such threshold has a value in the range of (1.2±0.5).

The term "allergen-specific immunotherapy" (AIT), as used herein, is a therapy wherein an allergen is administered repeatedly to a patient over a defined period of time. Typically, such allergen-specific immunotherapy comprises an initial phase wherein an allergen is administered repeatedly in increasing doses to a patient, wherein such doses of allergen increase up to a maximum dose that is effective to induce immunologic tolerance to said allergen in said patient. Such initial phase is herein also sometimes referred to as "up-dosing phase" or "initial induction phase". The amount of the maximum dose that is effective to induce immunologic tolerance in a patient can be easily determined by a person skilled in the art. Such a maximum dose typically is the dose that is effective to induce immunologic tolerance to said allergen in a patient and is therefore herein also sometimes referred to as "effective dose". In practice, usually, every established immunotherapy vaccine will have a summary of product characteristics (SPC) with a recommended maintenance dose. However, an allergologist can also easily determine an individual patient's threshold(s) by updosing to a limit, where systemic reactions occur. Nowadays for any immunotherapy vaccine, every manufacturer usually conducts dosage-finding studies in which maximum doses are determined, and these are usually indicated in the SPC and the product leaflet and can be followed in practice.

Typically, there are different types of allergen-specific immunotherapies which differ from each other in terms of their mode of administration of the allergen. In one example, such allergen-specific immunotherapy involves subcutaneous administration, i.e. typically injection of an allergen. Such allergen-specific immunotherapy involving subcutaneous administration is also sometimes referred to as subcutaneous immunotherapy or subcutaneous allergen immunotherapy or SCIT. In another example, such allergen-specific immunotherapy involves sublingual administration of the allergen. Such allergen-specific immunotherapy involving sublingual administration is also sometimes referred to as sublingual immunotherapy or sublingual allergen immunotherapy or SLIT.

In either form of allergen-specific immunotherapy, there is comprised an initial induction phase, wherein an allergen is repeatedly administered to a patient in increasing doses of said allergen ("up-dosing phase") up to a maximum dose effective to induce immunologic tolerance to said allergen in said patient, and thereafter follows a maintenance phase in such allergen-specific immunotherapy, wherein said allergen is administered repeatedly to said patient at said maximum dose. In one embodiment of the method according to the present invention, said ratio of cell counts is determined in the first 1-7 weeks of the maintenance phase after the initial induction phase. In one embodiment, this applies to both SCIT and SLIT.

Determination of cell counts and their respective ratio is done by taking sample(s) from the patient as defined herein, and determining cell counts and ratio from such sample(s).

In the subcutaneous immunotherapy, after the initial phase of increasing doses ("up-dosing phase") of allergen up to a maximum dose (during which initial phase the allergen is administered repeatedly, preferably weekly), typically there is a maintenance phase thereafter, wherein the allergen is administered repeatedly at the maximum dose. Typically, in such subcutaneous immunotherapy, the allergen is administered subcutaneously, preferably by way of an injection, of a solution or dispersion. Injections are preferably administered subcutaneously In one embodiment of such subcutaneous immunotherapy, the maintenance phase can be subdivided further into a first sub-phase, herein also sometimes referred to as "top-dose phase", wherein said allergen is administered at said maximum dose in defined intervals, preferably weekly or biweekly. Subsequently, there is a second subphase, herein also sometimes referred to as "treatment maintenance phase", wherein said allergen is administered repeatedly at the same maximum dose as in the top-dose phase, but in intervals longer than during the top-dose phase, preferably every 4-6 weeks. Hence, in one embodiment of the method according to the present invention, an allergen-specific immunotherapy involves a subcutaneous administration of allergen to a patient and comprises an initial induction phase of increasing doses of allergen administered weekly, a top-dose phase of maximum doses of allergen administered weekly or biweekly, and a treatment maintenance phase of maximum doses of allergen administered every 4-6 weeks. In such embodiments, the initial phase typically is for a period of 3-8 weeks, the top-dose phase is for a period of 1-4 weeks, and the treatment maintenance phase is for 1-3 years. In one embodiment, the initial phase may also be shortened due to the employment of an accelerated administration schedule (aka "rush scheme") in which either the frequency of the injections or the incremental dose increase between consecutive injections or both may be increased. Thus, accelerated schedules either involve administering more injections per visit/administration, increasing the dose more between consecutive injections, or both. If such an accelerated scheme is employed, the initial induction phase has a length of approximately 1-2 weeks, and the frequency of administration during such initial induction phase may be changed from weekly to daily or even shorter time intervals.

Preferably, in an embodiment of subcutaneous immunotherapy, comprising an initial induction phase of increasing doses of allergen administered weekly, a top-dose phase of maximum doses of allergen administered weekly or biweekly, and a treatment maintenance phase of maximum doses of allergen administered every 4-6 weeks, said ratio of cell counts is determined after administration of any maximum dose of said top-dose phase, preferably after administration of the last maximum dose of said top-dose phase. In one such embodiment, said ratio of cell counts is determined 4-10 hours after administration of any maximum dose of said top-dose phase, preferably 4-10 hours after administration of the last maximum dose of said top-dose phase.

In the sublingual immunotherapy (SLIT), after the initial phase of increasing doses ("up-dosing phase") of allergen up to a maximum dose, typically, there is a maintenance phase thereafter, wherein the allergen is administered repeatedly at the maximum dose. Typically, in such sublingual immunotherapy, the allergen is administered sublingually as a solution or dispersion. Drops are orally administered and may be kept by a patient sublingually ("under the tongue") for a defined period of time, e.g. 1-10 minutes, preferably 1-5 minutes, more preferably 1-3 minutes.

In one embodiment of such sublingual immunotherapy, in the initial induction phase, an allergen is repeatedly, preferably every other day, sublingually administered to a patient in increasing doses of said allergen up to a maximum dose effective to induce immunologic tolerance to said allergen in said patient, in the subsequent maintenance phase, said allergen is repeatedly, preferably daily, sublingually administered to said patient at said maximum dose. Hence, in one embodiment of the method according to the present invention, an allergen-specific immunotherapy involves a sublingual administration of allergen to a patient and comprises an initial induction phase of increasing doses of allergen administered every other day, and a maintenance phase of maximum doses of allergen administered daily. In such embodiments, the initial induction phase of increasing doses typically is for a period of 3-6 weeks, and the maintenance phase of maximum doses typically is for a period of 10-18 months. In one embodiment the total duration of the sublingual immunotherapy is 12-18 months, and the treatment schedule comprises a six-week up-dosing phase, involving administration of the allergen every other day, followed by a daily maintenance treatment during the maintenance phase. In one example of such SLIT, up-dosing involves three administrations of allergen per week, with increasing doses from week 1 to week 6 (as an example e.g. one drop of allergen solution administered per administration in week 1, two drops of allergen solution administered per administration in week 2, 4 drops of allergen solution administered per administration in week 3, and 7, 10 and 14 drops of allergen solution administered per administration in weeks 4, 5, and 6, respectively). In one embodiment of such SLIT, the maintenance phase involves a daily administration of the maximum dose, which had been achieved in the last week of up-dosing, as a maintenance dose.

Preferably, in an embodiment of sublingual immunotherapy, comprising an initial induction phase of increasing doses of allergen administered weekly, and a maintenance phase of maximum doses of allergen administered daily, said ratio of cell counts is determined after administration of any maximum dose of said maintenance phase during the first 1-7 weeks after the initial induction phase.

In one embodiment, AIT is timed such that the initial induction phase and the top-dose phase (in the case of SCIT), or the initial induction phase and the first 1-7 weeks of the maintenance phase (in the case of SLIT) are performed before the respective allergen occurs naturally in the environment, e.g. before the allergen is distributed naturally by its natural source, e.g. before pollination season. For example, if the allergen is birch pollen, AIT is performed such that the induction phase and the top-dose phase (in the case of SCIT), or the initial induction phase and the first 1-7 weeks of the maintenance phase (in the case of SLIT) are performed such that they are finished before birch pollen is distributed by birch trees in their natural habitat.

In one embodiment of the method according to the present invention involving a SCIT scheme, the determination of said ratio of cell counts of interleukin-10 producing regulatory B-cells and interleukin-17 producing T-helper cells is done after administration of any maximum dose in the top-dose phase, preferably after administration of the last maximum dose in the top-dose phase. The inventors have found that whilst such ratio seems to be of general value for predicting therapeutic success of an allergen specific immunotherapy (AIT), the determination after administration of any maximum dose in the top-dose phase is particularly suitable for predicting therapeutic success of the allergen-specific immunotherapy. The inventors have found that it is particularly useful for predicting therapeutic success if such determination is performed within 2-12 hours, preferably within 4-10 hours after the respective maximum dose has been administered.

In one embodiment of the method according to the present invention involving a SLIT scheme, the determination of said ratio, preferably said ratio of cell counts of interleukin-10 producing regulatory B-cells and interleukin-17 producing T-helper cells is done after administration of any maximum dose in the maintenance phase within the first 1-7 weeks of such maintenance phase, preferably after administration of any maximum dose in weeks 4-7 of such maintenance phase. The inventors have found that it is particularly useful for predicting therapeutic success if such determination is performed within 2-12 hours, preferably within 4-10 hours after the respective maximum dose has been administered.

The term "therapeutic success", as used herein is meant to refer to a state, wherein the symptoms of the allergic disease are reduced or absent in comparison to an allergen-exposed patient's status prior to said allergen-specific immunotherapy. In one preferred embodiment, therapeutic success is determined by a patient-assessed retrospective assessment of seasonal allergic symptoms (RAAS) by scoring overall disease symptoms, e. g. hay fever symptoms, in comparison to the season before the start of immunotherapy and in year 3 in comparison to the time prior to treatment. The score given by the patient is on a scale between +3 ("much better") to 0 ("no change") to −3 ("much worse"). Determination or measurement of therapeutic success by RAAS is known to a person skilled in the art and can for example be performed as described in A. M. Chaker et al., 2016, Journal of Allergy and Clinical Immunology, 137, pp. 452-461.

In another preferred embodiment, therapeutic success is determined or measured by a combined symptom medication score (CSMS) as e.g. described in Pfaar et al. 2014, Allergy; 69, pp. 854-867, or by visual analog scale (VAS) as e.g. described in Pfaar et al. 2014, Allergy; 69, pp. 854-867, making use of exposure chambers.

As used herein, the term "a patient suffering from an allergic disease" is meant to refer to a patient who, upon exposure to an allergen, develops or has developed symptoms of said allergic disease; but such term should also be understood as including a patient who, prior to exposure to said allergen, is nevertheless likely or prone to develop such symptoms upon exposure to the allergen. This can for example be, because it is clear from a patient's history that (s)he has had attacks of such allergic disease in earlier times, for example during the flowering period of specific plants in previous year(s) or seasons. The term is also meant to include patients who have a known disposition to develop symptoms of an allergic disease or a family history of symptoms of an allergic disease, but have not yet developed such disease in the present allergen season.

The term "allergen", as used herein, is meant to refer to a wide range of substances or agents, such as plant pollen, in particular tree pollen, such as from birch, alder, poplar, elm, willow, oak, maple, ash, hazel, and beech, grass pollen (Poaceae), such as pollen from species like *Phleum pratense, Lolium perenne, Dactylis glomerata, Holcus lanatus, Poa pratensis, Festuca pratensis, Cynodon dactylon, Paspalum notatum, Anthoxanthum odoratum* and rye (*Secale cereale*), weed pollen, such as from nettle(s), ragweed, mugwort, plantain other airborne particles, such as mould spores, mites, animal dander, fungi and fungal spores, but also venom from insects such as bees or wasps As an example, as allergen(s) a mixture of grass pollen can be used, e.g. pollen from *Holcus lanatus, Dactylis glomerata, Lolium perenne, Phleum pratense, Poa pratensis*, and *Festuca pratensis*.

Numerous preparations of allergens are commercially available, e.g., Allergovit® 6-grasses (Allergopharma GmbH & Co. KG, Reinbek, Germany), a 100% mixture of allergens from 6 grass pollen species (*Holcus lanatus, Dactylis glomerata, Lolium perenne, Phleum pratense, Poa pratensis*, and *Festuca pratensis*) chemically modified with formaldehyde to produce an allergoid, which is then co-precipitated with aluminium hydroxide, was used. Allergovit® 6-grasses is specified in therapeutic units per mL (TU/mL), provided in two strengths (A: 1000 TU/mL and B: 10,000 TU/mL).

The term "gene expression signature", as used herein refers to a gene or a pattern of genes that shows an expression that is typical for a particular cell. For example, the gene expression signature of IL-10$^+$ Bregs is a set of genes that is expressed in a specific characteristic manner and is thus typical for such cells.

In one embodiment, the ratio, preferably the ratio of cell counts, of interleukin-10 producing regulatory B-cells (IL-10$^+$ Bregs) to the cell count of interleukin-17 producing T-helper cells (Th17) is herein also sometimes referred to as "IL-10$^+$ Bregs/Th17". It has turned out that such ratio is a particularly good indicator for predicting therapeutic success of an allergen-specific immunotherapy in a patient suffering from an allergic disease. In one embodiment, it is preferred that the cell counts of interleukin-10 producing regulatory B-cells (IL-10$^+$ Bregs) and of interleukin-17 producing T-helper cells (Th17) are relative cell counts wherein said relative cell count of IL-10$^+$ Bregs cells is determined as number of IL-10$^+$ Bregs with reference to the number of live CD19$^+$ B-cells in a sample from said patient, and said relative cell count of Th17 cells is determined as number of Th17 cells with reference to the number of live CD4$^+$ CD3$^+$ T-cells in a sample from said patient. The ratio IL-10$^+$ Bregs/Th17 then is the ratio of such relative cell counts. It is preferred that the respective relative cell counts are determined in two separate samples, which however have been taken at the same point in time from the patient. Preferably they are determined in in/from two different stainings in two separate samples taken at the same time from the patient. The present inventors have found that if such ratio equals or exceeds a defined threshold, it is likely that an allergen-specific immunotherapy will be successful in such patient. If the ratio is below such defined threshold, it is likely, that an allergen-specific immunotherapy will not be successful in said patient. Because, in a preferred embodiment, the ratio of these cell counts is determined relatively early during the allergen-specific immunotherapy, namely during the induction phase with increasing doses or during the first 2-8 weeks of the subsequent maintenance phase, for example after administration of the last maximum dose during the top-dose phase, it can then already be decided whether or not to continue with such allergen-specific immunotherapy, based on a prediction of therapeutic success using the aforementioned ratio.

In one embodiment, the ratio, preferably the ratio of cell counts, is determined in one or several samples obtained from the patient. Typically, such sample(s) is/are selected from whole blood, peripheral blood mononuclear cells (PBMCs), nasal cells obtained from nasal scrapings or a nasal biopsy of said patient, bronchial cells obtained from sputum, from a lung biopsy or from bronchial alveolar lavage fluid (BALF) of said patient. In one embodiment, such ratio is determined in all of the aforementioned samples. In another embodiment, only a subset of samples is used for determining the ratio, preferably the ratio of cell counts. As an example, a ratio of gene expression signatures or cell counts may be determined in whole blood samples and in bronchial cells, or in only a subset of blood samples taken at any particular point in time.

In one embodiment, determination of cell counts is achieved by flow cytometry, fluorescence-activated cell sorting (FACS), determining cell counts by means of a Coulter counter, haemocytometer, image analysis or spectrophotometry.

In one embodiment, said method of predicting therapeutic success additionally includes a step of determining in a blood sample/nasal scraping sample, the expression level of one or several markers selected from Bregs will be set in relation to those of Th17 cells, wherein an higher expression of Breg genes (eg IL-10) in ratio to low Th17 cells (eg. RORC2 or IL-17) is indicative of therapeutic success.

In one embodiment, the method of predicting therapeutic success of an allergen-specific immunotherapy is an ex-vivo method. In one embodiment, the allergen-specific immunotherapy (AIT) is not part of the method of predicting therapeutic success. Hence, the method of predicting therapeutic success is not practiced on the human (or animal) body and is performed in-vitro or ex vivo, using samples obtained from a patient for whom therapeutic success or non-success of an allergen-specific immunotherapy is to be predicted. In one embodiment, the patient is a human being. In another embodiment, the patient is a non-human animal, preferably a non-human mammal.

The present invention also relates to the use of a a method for predicting therapeutic success of an allergen-specific immunotherapy (AIT) in a patient suffering from or having a disposition to develop an allergic disease, wherein such method comprises determining a ratio of gene expression signatures or cell counts, IL-10 Bregs/Th17, as defined above and predicting success or nonsuccess of an allergen-specific immunotherapy in said patient, based on such determined ratio. In this method, the patient, the allergen-specific immunotherapy, the ratio of gene expression signatures or cell counts etc. are as already defined above.

In a further aspect, the present invention also relates to a kit
   for predicting therapeutic success of an allergen-specific immunotherapy (AIT) in a patient suffering from or having a disposition to develop an allergic disease selected from hay fever, allergic rhinitis, allergic asthma, allergic conjunctivitis, food allergy and stinging insect hypersensitivity, said kit comprising:

Means to obtain a sample from said patient suffering from or having a disposition to develop an allergic disease, said sample being selected from whole blood, peripheral blood mononuclear cells (PBMCs), nasal cells obtained from nasal scrapings or a nasal biopsy of said patient, bronchial cells obtained from sputum, a lung biopsy or bronchial alveolar lavage fluid (BALF) of said patient;

means to perform a quantitative determination of gene expression signatures or cell counts of interleukin-10 producing regulatory B-cells (IL-10$^+$ Bregs) and interleukin-17 producing T-helper cells (Th17) in said sample, wherein said cell counts of IL-10$^+$ Bregs and Th17 are relative cell counts, wherein said relative cell count of IL-10$^+$ Bregs cells is determined as number of IL-10 Bregs with reference to the number of live CD19$^+$ B-cells, and wherein said relative cell count of Th17 cells is determined as number of Th17 cells with reference to the number of live CD4 CD3 T-cells.

In one embodiment, the kit according to the present invention further comprises:

Means to determine a ratio of gene expression signatures or cell counts of IL-10$^+$ Bregs and Th17, namely IL-10$^+$ Bregs/Th17.

In one embodiment, the kit according to the present invention further comprises:

A set of instructions for use of said kit, said instructions indicating a threshold, wherein, if a determined ratio is ≥ said threshold, such ratio indicates therapeutic success of an allergen-specific immunotherapy, and if a determined ratio is < said threshold, such ratio indicates no therapeutic success of an allergen-specific immunotherapy.

In one embodiment, said ratio is a ratio of cell counts and said threshold is 1.2.

Moreover, the present invention is now further described by reference to the following examples which are given to illustrate, not to limit the present invention.

EXAMPLES

Example 1—Materials and Methods

Study design. In this study, the present inventors report data from our Prospective Allergy and Clinical Immune Function Cohort study (PACIFIC, EudraCT 2015-003545-25), an open and ongoing observational allergy cohort. Patent characteristics can be found in the following table:

Characteristics of the Patients in the PACIF Cohort

| Characteristic | Immunotherapy Group n = 68 | Untreated Allergic Controls n = 19 | Non-Allergic Controls n-21 |
|---|---|---|---|
| Age (years)* | 25.31 ± 5.47 | 31.00 ± 8.08 | 26.95 ± 4.90 |
| Male sex (%) | 29 (50%) | 12 (39%) | 8 (38%) |
| Sensitization (%) | | | |
| Grass | 100% | 100% | 0% |
| Birch | 40% | 60% | 0% |
| House Dust Mite | 30% | 50% | 0% |
| Allergic Asthma | 18 (32%) | 9 (26%) | 0% |

Plus-Minus Values Indicate SD
*at informed consent procedure and inclusion into study For this analysis, 58 mono-symptomatic grass-pollen allergic patients underwent subcutaneous grass-pollen AIT with a grass-pollen allergoid (Allergovit®, Allergopharma GmbH & Co. KG, Germany) consisting of a 100% mixture of allergens from six grass pollen species (*Holcus lanatus, Dactylis glomerata, Lolium perenne, Phleum pratense, Poa pratensis*, and *Festuca pratensis*) chemically modified with formaldehyde and alum absorbed and an overall major allergen content of 25 µg per maintenance dose as described recently (36). The study was approved by the ethics commission of the Technical University of Munich (5534/12). After written and informed patients' consent and in accordance with the Helsinki declaration, peripheral blood was obtained from patients at specific time points—at baseline levels, right before and 6 hours after the first and the last pre-seasonal top dose injection in year one of AIT. All laboratory tests were conducted with blinded study personnel. Following the initial treatment phase, patients were treated with follow-up AIT injections every 4-6 weeks over a period of three years with reduction of the maintenance dose during grass-pollen season depending on symptom burden. Further blood samples were taken twice a year, once in (May-July) and once out of grass pollen season (November-March). Samples size of 11 patients that were monitored at all timepoints resulted from self-limiting availability due to drop-outs or missed visits of study patients during the longitudinal study over three years. Outcome was measured by patient-assessed Retrospective Assessment of seasonal Allergic Symptoms (RAAS) by scoring overall hayfever symptoms in comparison to the season before and in year 3 in comparison to prior to treatment on a scale between +3 (much better), to 0 (no change) to −3 (much worse) (29). (Chaker et al. 2016 Journal of allergy and clinical immunology, 137, pp. 452-461)

Primary human nasal samples. Following written and informed patients' consent, nasal scrapings were performed in the Allergy Section, Department of Otolaryngology, TUM School of Medicine (Munich, Germany). For nasal flow cytometric analysis in peak pollination season 2016, not all included patients in the immunotherapy group had already received full three years of specific immunotherapy. Eleven healthy individuals served as control group and were compared to eight grass pollen-allergic patients without AIT and eleven grass pollen-allergic patients treated with grass-pollen AIT.

Culture conditions. For T cell flow cytometric analyses, primary PBMCs were cultured in RPMI supplemented with 10% fetal bovine serum (GE Healthcare Life Sciences, Buckinghamshire, UK), 50 IU/ml penicillin/streptomycin, 2 mM L-glutamine and 1× antibiotic/antimycotic (Gibco, Carlsbad, CA, USA) at 37° C. and 5% $CO_2$ in a fully-humidified atmosphere and stimulated using 10 ng/ml PMA, 1 µg/ml ionomycin, and 5 µg/ml brefeldin A (Sigma-Aldrich, St. Louis, MO, USA) for four hours. For B cell analysis, primary PBMCs were cultured in RPMI supplemented with 10% human serum (Sigma-Aldrich, St. Louis, MO, USA), 50 IU/ml penicillin/streptomycin, 2 mM L-glutamine and 1× antibiotic/antimycotic (Gibco, Carlsbad, CA, USA) at 37° C. and 5% $CO_2$ in a fully-humidified atmosphere for four hours. Following the four-hour incubation period, cells were labeled for flow cytometry.

Stimulation with phleum major antigen. PBMCs were cultured in serum-free CTL-Test B™ Medium (Cellular Technology Ltd., Shaker Heights, OH, USA) supplemented with 2 mM L-glutamine at a density of 4 million PBMCs/ml and stimulated with either 5 µg/ml phleum (recombinant phleum p1, Allergopharma GmbH & Co. KG, Reinbek, Germany) or a specialized B-Poly-SE B cell stimulant (Cellular Technology Ltd, Shaker Heights, OH, USA) at 37°

C. and 9% $CO_2$ in a fully humidified atmosphere for 7 days according to manufacturer's instructions. Cells were subjected to flow cytometric analysis, supernatants were concentrated to a 10-fold concentration by centrifugation through protein-binding Amicon columns (Merck Millipore, Millerica, MA, USA) and subjected to ELISA or MSD Mesoscale analysis.

Flow cytometry. Following specific stimulation regimes, PBMCs were labeled for flow cytometry with specific antibodies using the Foxp3/Transcription Factor Staining Buffer Set (eBioscience, San Diego, CA, USA) according to manufacturer's instructions. Flow cytometric analysis was performed using a BD LSRII FACSFortessa flow cytometer (BD, Franklin Lakes, NJ, USA). Flow cytometry data were analyzed with FlowJo software (FlowJo, Ashland, OR, USA). Antibodies used for flow cytometry are listed in the following table:

SUPPLEMENTARY TABLE 2

Fluorochrome-labelled antibodies used in flow cytometry analyses

| Antigen | Fluorochrome | Company | Clone |
|---|---|---|---|
| CD1d | PercP-Cy5.5 | BioLegend | 51.1 |
| CD3 | PercP-Cy5.5 | BD | UCHT1 |
| CD3 | APC-Cy7 | BioLegend | HIT3a |
| CD4 | V450 | BD | RPA-T4 |
| CD4 | PE-Dazzle 594 | BioLegend | A161A1 |
| CD5 | FITC | BioLegend | UCHT2 |
| CD19 | Brilliant Violet 605 | BD | SJ25-C1 |
| CD19 | APC-Cy7 | BioLegend | HIB19 |
| CD24 | PE-CF594 | BD | ML5 |
| CD27 | Brilliant Violet 711 | BioLegend | O323 |
| CD27 | Brilliant Violet 605 | BioLegend | O323 |
| CD38 | Brilliant Violet 605 | BioLegend | HB-7 |
| CD45RA | eFluor780 | ebioscience | HI100 |
| PD-L1 (CD274) | Brilliant Violet 650 | BD | MIH1 |
| IFN-γ | APC | BioLegend | 4S.B3 |
| IL-4 | Alexa Fluor 488 | BD | 8D4-8 |
| IL-10 | PE | ebioscience | JES3-9D7 |
| IL-13 | APC | BD | JES10-5A2 |
| IL-17A | Brilliant Violet 711 | BioLegend | BioLegend 168 |
| FoxP3 | APC | ebioscience | PCH101 |
| FoxP3 | PE | ebioscience | PCH101 |
| TNF-α | V450 | BD | MAb11 |

RNA isolation and whole genome microarray. As described before, total RNA was extracted using RNeasy Mini Kit (Qiagen, Hilden, Germany) with on-column DNase digestion (Qiagen) for avoiding DNA contaminations (34). RNA quantification was performed by ultraviolet-visible spectrophotometry (Nanodrop Technologies, Wilmington, DE), for assessment of the RNA integrity by the RNA 6000 Nano Chip Kit with the Agilent 2100 Bioanalyzer (Agilent Technologies, Waldbronn, Germany). Total RNA was amplified and Cy3-labeled by using the one-color Low Input Quick Amp Labeling Kit (Agilent Technologies) according to the manufacturer's protocol. Hybridization to SurePrint G3 Human Gene Expression 8×60K Microarrays (Agilent Technologies) was performed with the Gene Expression Hybridization Kit (Agilent Technologies).

Microarray data analysis strategy. Upon data import a standard baseline transformation to the median of all values was performed, including log transformation and computation of fold changes. Subsequently, a principle component analysis (PCA) was conducted and revealed a homogenous component distribution. Compromised array signals (array spot is non-uniform if pixel noise of feature exceeds threshold or above saturation threshold) were excluded from further analysis. Genes with an absolute log 2 fold change larger than 1.5 and a corrected p-value smaller than the testing level of 0.05 by using the Moderated T-Test were defined as significantly differentially expressed hits. Manhattan cityblock on entities (Ward's linkage) was used to cluster changes in gene expression.

Enzyme-linked Immunosorbent Assay (ELISA). ELISA was performed on conditioned supernatants from PBMC cultures using Human IgG4 or IgE ELISA Ready-SET-Go! Kits (eBioscience, San Diego, CA, USA) according to manufacturer's instructions. Absorption was visualized using an ELISA reader (Epoch™ spectrophotometer, BioTek Instruments, Inc., Winooski, VT, USA).

ImmunoCAP test. Grass pollen-specific IgE and IgG4 serum levels were analyzed by the standardized diagnostic ImmunoCAP test (Phadia Thermo Scientific, Uppsala, Sweden), which determines antigen-specific IgE and IgG4 antibodies in the serum. The test principle is based on a sandwich immunoassay with high binding capacity of relevant immunoglobulins.

Data acquisition and Statistical analysis. All experimental procedures and analysis were conducted by blinded research staff. Data are included in parenthesis throughout the results section as mean±s.e.m. Two-sided Wilcoxon-rank sum tests were used to test for significant differences sequential data points of the same patient. Two-sided Mann-Whitney tests were used to determine significant differences between patient groups. Statistically significant differences were defined asp values *$p<0.05$, $p<0.01$, *$p<0.001$, ****$p<0.0001$.

Example 2—Increase of Regulatory B-Cells Following an Initial Allergen-Specific Immunotherapy Coincides with a Reduction of Th1 and Th17 Cell Counts During Pre-Seasonal Up-Dosing in Year 1

Here, the present inventors prospectively monitored grass pollen-allergic patients during a longitudinal allergen immunotherapy (AIT) study in order to characterize the immediate and long-term immune response to grass pollen AIT in the periphery and in the upper airways. Following an initial treatment phase using a standard AIT up-dosing scheme and three subsequent top dose injections, patients further obtained maintenance shots every four to six weeks over a period of three years (FIG. 1A). A complex sampling procedure during treatment course was chosen to assess allergen-induced immediate local and systemic immune reactions, including time points right before and six hours after initial pre-seasonal top dose injections. During the observation phase, the present inventors analyzed samples in and out of grass pollen season to comprise the natural allergen-stimulating effect of grass pollination.

FIG. 1 shows that an increase of regulatory B-cells following an initial allergen-specific immunotherapy (AIT) coincides with a reduction of Th1 and Th17 cell counts during pre-seasonal up-dosing in year 1. More specifically, FIG. 1 shows the following:

(A) Study design of the open-label Prospective Allergy and Clinical Immune Function Cohort (PACIFIC). Following a pre-seasonal weekly up-dosing phase, grass pollen-allergic patients were treated biweekly with three top dose injections of a standard grass pollen-specific immunotherapy (top-dose phase). During the follow-up treatment phase (treatment maintenance phase), maintenance dose of 25 μg of grass group 5 allergens was applied monthly with seasonal dosage adaption according to symptom burden throughout an observation period of three years. Samples were taken at the specific time points A—Baseline, B—right before the first initial top dose, C—6 h after the first initial top dose, D—right before the last initial top dose, E—6 h after the last initial top dose, F—in grass pollen season year 1 of follow-up treatment phase, G—out of grass pollen season (=off season) year 1, H—in grass pollen season year 2 of follow-up treatment phase, I—out of grass pollen season (=off season) year 2, K—in grass pollen season year 3 of follow-up treatment phase. Analysis of systemic T and B cell subsets using intracellular cytokine staining and subsequent flow cytometry comparing time points A—Baseline and E—6 h after last top dose (n=20 PBMC patient samples per group): (B) IL-4$^+$ CD4$^+$ Th2 cells; (C) IFN-γ$^+$ CD4$^+$ Th1 cells; (D) IL-17$^+$ CD4$^+$ Th17 cells; (E) FoxP3$^+$ regulatory CD4$^+$ T cells; (F) IL-17$^+$/FoxP3$^+$-co-expressing CD4$^+$ Tr17 cells; (G) total CD19$^+$ B cell numbers; (H) CD27$^+$ memory B cells; (I) IL-10$^+$ regulatory B cells. Data are depicted as scatter plots showing all data points and median. (J) Identification of a subgroup of patients, which up-regulates Breg cell numbers following the initial treatment phase. (K) Depiction of changes in the Th1 and Th17 frequencies of the selected subset from (J). (L) Correlation of Breg frequencies with Th1 cell numbers of all data points (A and E). (M) Correlation of Breg frequencies with Th17 cell numbers of all data points (A and E). Two-sided Wilcoxon-rank sum tests were used to test for significant differences between treatment time points. Statistically significant differences were defined asp values *p<0.05, p<0.01, *p<0.001, ****p<0.0001.

The early treatment phase showed an initial induction of a Th2 phenotype (A: 45.02%±5.06 vs. E: 59.87%±5.08; p<0.05; FIG. 1B) while Th1 (A: 2.62%±0.51 vs. E: 1.64%±0.34; p=0.055) and Th17 (A: 0.85%±0.10 vs. E: 0.55%±0.05; p<0.001) cells were significantly reduced in the peripheral blood of AIT patients (FIG. 1C,D). Whereas the regulatory FoxP3$^+$ T cell (Tregs) compartment remained unchanged at this early time point, a modest but significant increase of total and regulatory IL-10-producing B cells (Bregs) occurred (A: 1.90%±0.31 vs. E: 3.20%±0.75; p<0.05; FIG. 1E,G,I) while at the same time, an opposing trend in the memory B cell subset (A: 20.30%±1.86 vs. E: 16.36%±1.64; p<0.05; FIG. 1H) was observable. Notably, the present inventors discovered a significant decrease following initial AIT of the recently described population of IL-17-expressing CD4$^+$FoxP3$^+$ T cells (here called Tr17 cells) in the peripheral blood (A: 1.50%±0.22 vs. E: 0.95%±0.13; p<0.05; FIG. 1F). IL-10 induction in B cells correlated with a simultaneous decrease of peripheral Th1 (r=−0.56; p<0.001) and Th17 cells (r=−0.35; p<0.05; FIG. 1L,M), in particular a patient subgroup characterized by an increase of IL-10$^+$ Bregs showed a significant decrease of Th1 (A: 2.78%±0.52 vs. E: 0.79%±0.17) and Th17 cells (A: 0.86%±0.12 vs. E: 0.43%±0.06; FIG. 1J,K), supporting the well-established notion of the suppressive effects of Bregs on these Th subsets.

Figure 2:
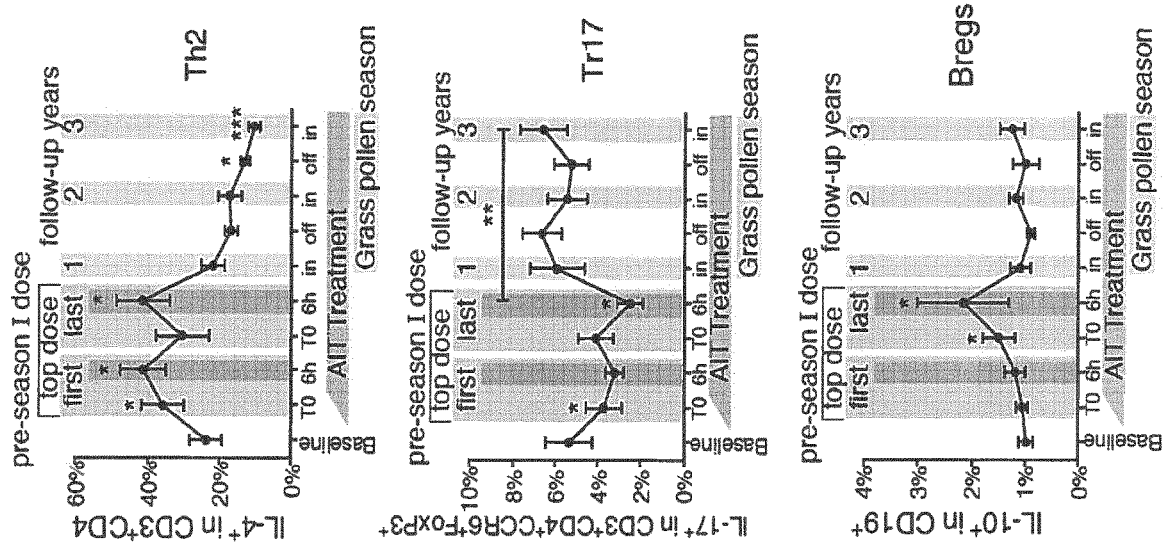
FIG. 2 shows longitudinal changes in immune subsets during the course of treatment: An initial allergen-specific immunotherapy induces IL-10-producing B- and T-cells.
Figure 2:
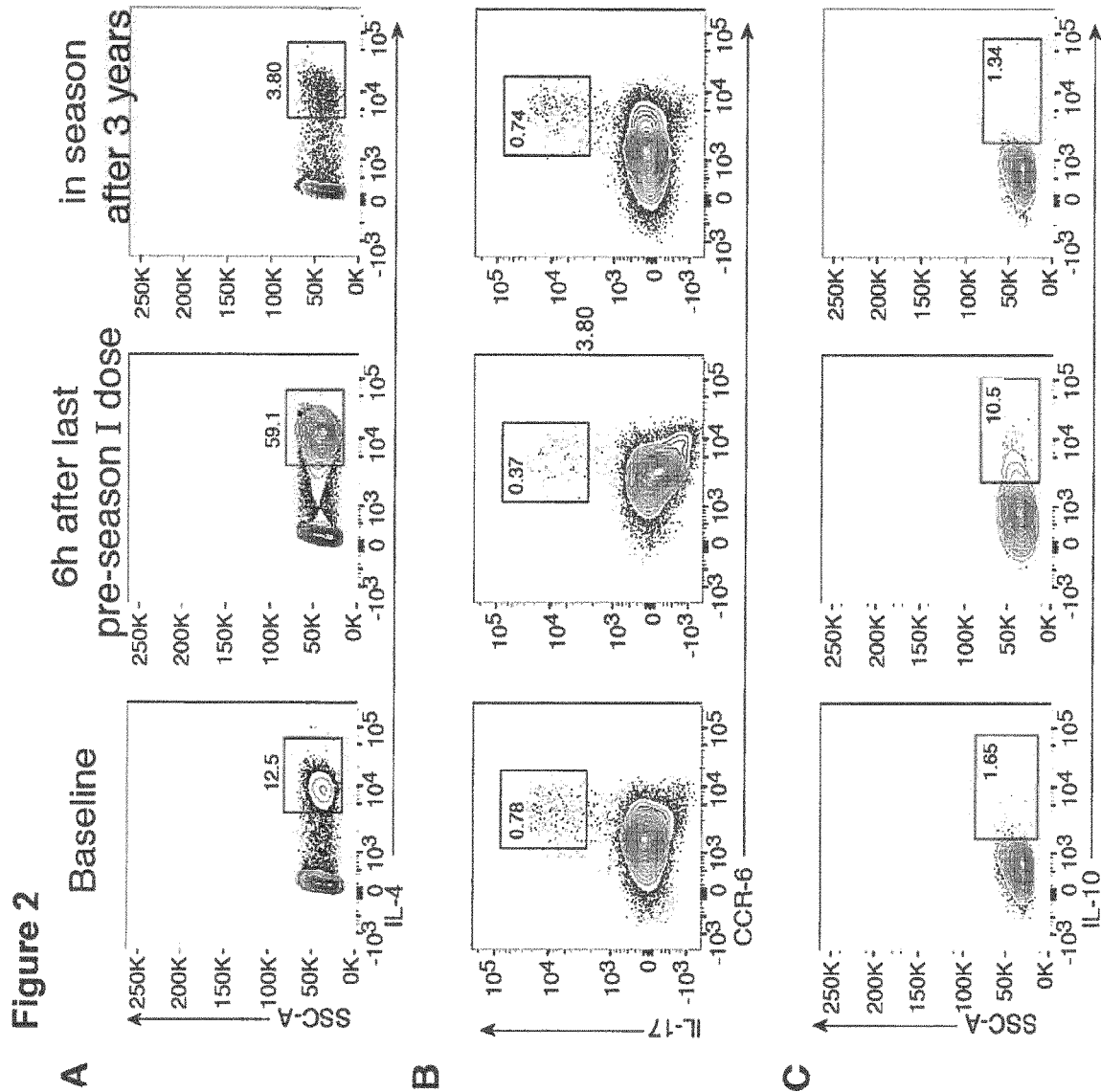

Example 3—Longitudinal Changes in Immune Subsets During Course of Treatment: Initial AIT Induces IL-10-Producing B- and T-Cells FIG. 2 shows: Longitudinal changes of circulating immune cell subsets were analyzed by intracellular flow cytometry including all time points of the PACIFIC study (n=11 patients; except time point I n=8). (A) IL-4$^+$ CD4 Th2 cells; (B) IL-17$^+$/FoxP3$^+$-co-expressing CCR6$^+$CD4$^+$ Tr17 cells. (C) regulatory B cells identified by IL-10 production. Dot plots show flow cytometry staining comparing time points A, E and K. (D) IFN-γ$^+$ CD4$^+$ Th1 cells; (E) IL-17$^+$ CD4$^+$ Th17 cells; (F) FoxP3$^+$ regulatory CD4$^+$ T cells; (G) IL-10-producing FoxP3$^+$ Treg cells; (H) CD27$^+$ memory B cells; (I) IL-10-producing CD27$^+$ memory B cells. Results are depicted as mean±s.e.m. Significances are calculated in comparison to baseline, if not otherwise indicated. Two-sided Wilcoxon-rank sum tests were used to test for significant differences between treatment time points. Statistically significant differences were defined as p values *p<0.05, p<0.01, *p<0.001, ****p<0.0001. Graphic abstraction shows a schematic overlay of the behavior of the counter populations (J) Bregs (black) versus Th17 cells (red) and (K) of Tregs (black) versus Th2 cells (red) during the three AIT phases 1) Initial up-dosing phase, 2) Conversion phase and 3) Tolerance mounting phase in order to depict their inverse course throughout long-term treatment.

Following the initial boost, the Th2 response continuously decreased throughout the three year maintenance phase reaching significant reduction in comparison to baseline only during the last year of AIT (A: 23.67%±4.50 vs. K: 10.43%±1.51; p<0.05; FIG. 2A,K). Surprisingly, the present inventors found a significant decrease of Th17 cells (A: 1.37%±0.30 vs. E: 0.97%±0.16; p<0.05) and CCR6$^+$ Tr17 cells (A: 5.36%±1.08 vs. E: 2.52%±0.59; p<0.05) in the periphery following initial AIT, thus showing inverse dynamics in comparison to Th2 cells (A: 23.67%±4.50 vs. E: 41.50%±7.64; p=0.001; FIG. 2B,E,J). The frequencies were restored in the first subsequent grass pollen season. Tr17 phenotype is stabilized at a significantly level over time in comparison to initial treatment (A: 5.36%±1.08 vs. K: 6.58%±1.13; p<0.01; FIG. 2B). Interestingly, Th17 cells showed an analogue pattern to Tr17 cells during up-dosing with a pronounced tendency to seasonal decrease (FIG. 2E). According to current understanding, the present inventors further found a significant increase of tolerogenic FoxP3$^+$ regulatory T cells, but only after three years of follow-up treatment (A: 3.09%±0.40 vs. K: 4.06%±0.32; p<0.01; FIG. 2F,K). Notably, during the up-dosing phase, regulatory B cells increased progressively (A: 0.99%±0.13 vs. E: 2.16%±0.84; p<0.05), but vanished quickly at the first pollen season (FIG. 2C,J). The induced regulatory B cell subset is phenotypically characterized by CD1dCD5$^+$ surface markers, while the proportion of CD24$^+$CD27$^+$ is decreasing throughout initial AIT (data not shown). Similar effects were observed in IL-10-producing Tregs (A: 10.06%±1.71 vs. E: 22.46%±4.27; p<0.05; FIG. 2G). In addition, the present inventors could found an initial slack of CD27$^+$ memory B cells (A: 15.02%±1.45 vs. C: 12.52%±1.38; p<0.05) with subsequent build-up during the maintenance phase, reaching significance compared to initial treatment effects only after three years (E: 12.38%±1.58 vs. K: 17.33%±1.92; p<0.01; FIG. 2H). Finally, CD27$^+$ memory B cells increased their IL-10 production early (A: 0.80%±0.11 vs. E: 1.26%±0.15; p<0.05) and maintained an increased level throughout the three-year follow-up (FIG. 2I).

Figure 3:
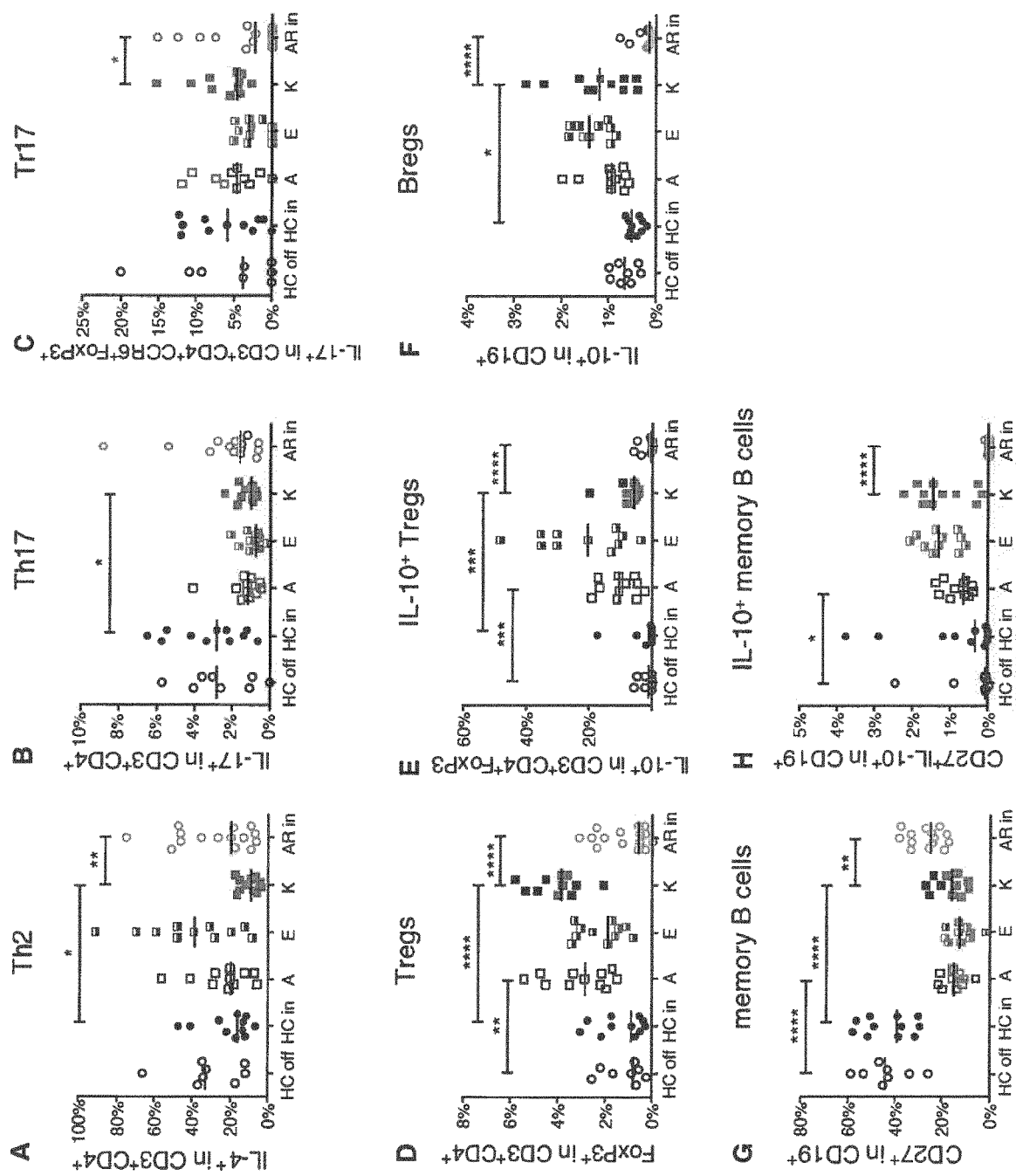
FIG. 3 shows differential long-term systemic therapy effects on Th17 and Tr17 subsets.

Example 4—Differential Long-Term Systemic Therapy Effects on Th17 and Tr17 Subsets FIG. 3 shows an intracellular flow cytometry analysis of circulating T and B cell subsets comparing healthy control subjects during off season (HC off; n=8), in grass pollen season (HC in; n=11), treated patients throughout course of therapy at time points A (Baseline), E (six hours after last initial top dose injection), and K (last in season after three years of follow-up) (n=11), untreated allergic rhinitis patients in grass pollen season (AR in; n=15): (A) IL-4$^+$ CD4$^+$ Th2 cells; (B) IL-17$^+$ CD4$^+$ Th17 cells; (C) IL-17$^+$/

FoxP3$^+$-co-expressing CCR6$^+$ CD4$^+$ Tr17 cells; (D) FoxP3$^+$ Treg cells; (E) IL-10-producing FoxP3$^+$ Treg cells; (F) IL-10$^+$ regulatory B cells; (G) CD27$^+$ memory B cells; (H) IL-10-producing CD27$^+$ memory B cells. Data are depicted as scatter plots showing all data points and median. Two-sided Mann-Whitney T-tests were used to test for significant differences between patient groups. Statistically significant differences were defined as p values *p<0.05, p<0.01, *p<0.001, ****p<0.0001.

Comparing longterm-treated (K) and untreated (AR in) grass pollen-allergic patients in season, as expected, circulating Th2 levels (untreated: 28,77%±5.35 vs. treated: 10.43%±1.51; p<0.01) were significantly decreased (FIG. 3A), whereas Th17 showed only a slight downward trend between groups (untreated: 2.38%±0.56 vs. treated: 1.27%±0.16; p=0.12) following AIT (FIG. 3B). However, significant AIT induced a significant increases of CCR6$^+$ Tr17 cells (untreated: 3.75%±1.31 vs. treated: 6.58% 1.13; p<0.05; FIG. 3C) and regulatory T cells (untreated: 1.23%±0.26 vs. treated: 4.06%±0.32; p<0.0001; FIG. 3D) where detectable compared to untreated controls. In addition, the present inventors found a strong systemic increase of IL-10 production in Tregs (untreated: 1.13%±0.50 vs. treated: 7.51%±1.34; p<0.0001) as well as in B cells (untreated: 0.22%±0.05 vs. treated: 6.09%±0.71; p<0.0001) comparing treated to untreated patients (FIG. 3E,F). A reduction of memory B cells was observed during immunotherapy, but not in untreated patients nor in healthy individuals (untreated: 26.84%±1.88 vs. treated: 17.07%±1.92; p<0.01), while IL-10$^+$ memory B cells were significantly increased throughout therapy if compared to untreated control patients (untreated: 0.01%±0.01 vs. treated: 1.21%±0.21; p<0.0001). This pattern of exclusively treatment-dependent alterations of cell populations was also observed for Th17 and memory B cells, which are below levels of healthy subjects or even untreated allergic rhinitis patients (FIG. 3B,G).

Example 5—Allergen-Specific Lymphocyte Activation in Favor of Immune Regulation

Figure 4:
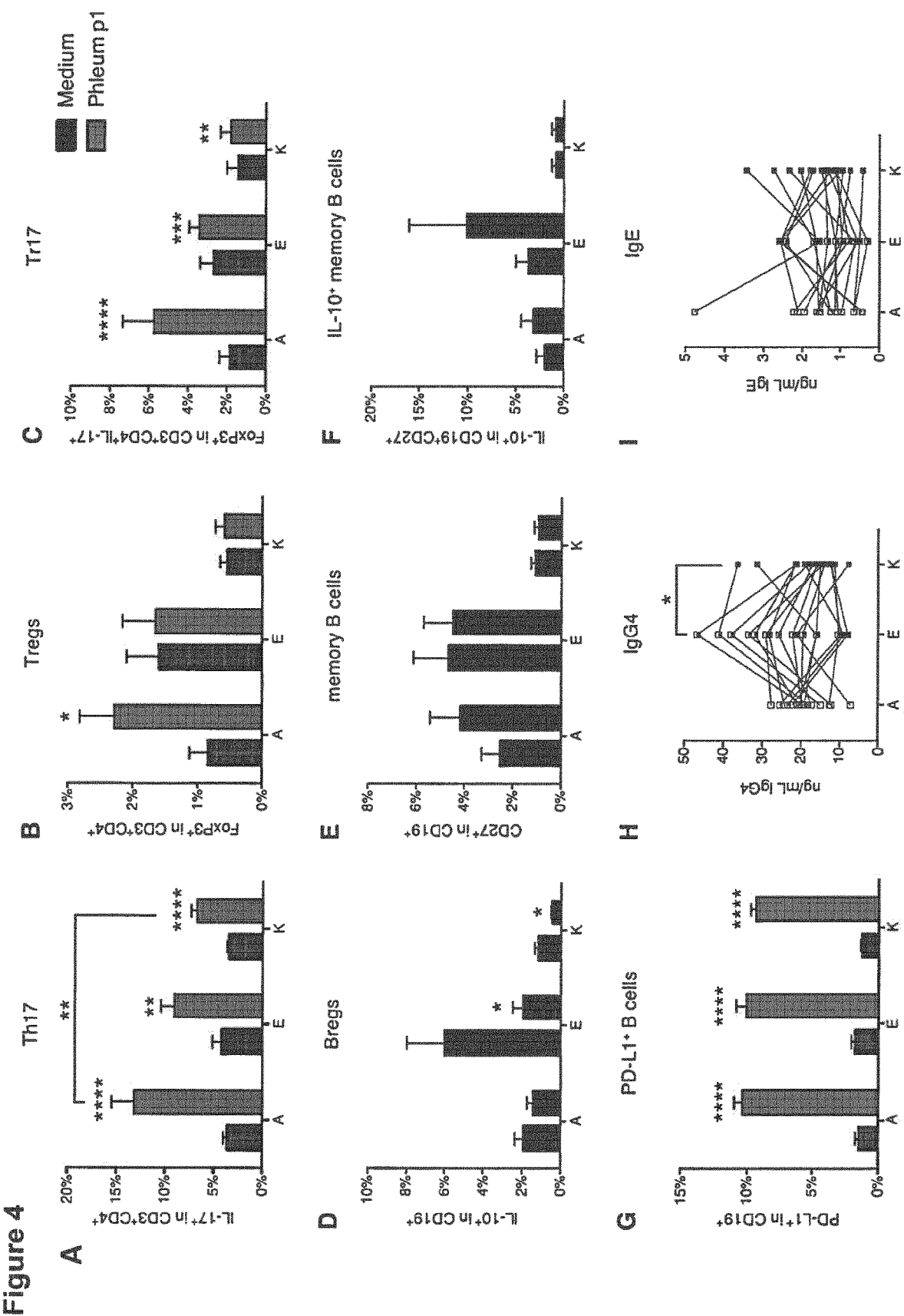
FIG. 4 shows that an allergen-specific lymphocyte activation is in favor of immune regulation.

FIG. 4 shows PBMCs from 17 patients throughout therapy course time points A (Baseline), E (six hours after last initial top dose injection), K (last in season after three years of follow-up) were stimulated with medium (black) or 5 μg/ml phleum p1 (red) for 7 days in culture and T and B cell subsets were analyzed using intracellular antigen staining: (A) IL-17$^+$ CD4$^+$ Th17 cells; (B) FoxP3$^+$ Treg cells; (C) IL-17$^+$/FoxP3$^+$-co-expressing CD4$^+$ Tr17 cells; (D) IL-10$^+$ Bregs; (E) CD27$^+$ memory B cells; (F) IL-10-producing CD27$^+$ memory B cells; (G) PD-L1$^+$ B cells. Results are depicted as mean±s.e.m. Significances are calculated in comparison to medium/untreated, if not otherwise indicated. Two-sided Mann-Whitney T-tests were used to test for significant differences between sample groups. Immunoglobulin secretion was determined by supernatant analysis using IgG4 (H) and IgE (I) ELISA following medium (data not shown) or phleum p1 stimulation for 7 days at the same time points A, E, and K.

Samples from the same patient are connected. Two-sided Wilcoxon-rank sum tests were used to test for significant differences between treatment time points. Statistically significant differences were defined asp values *p<0.05, p<0.01, *p<0.001, ****p<0.0001.

Following in vitro antigen challenge assays of patient PBMCs for seven days with major grass pollen allergen phleum p1, the present inventors found a significant induction of IL-17-producing CD4$^+$ T cells at baseline (medium: 3.56%±0.41, phleum: 13.22%±2.28; p<0.0001) (FIG. 4A). The antigen-specific induction of Th17 cells was strongly decreased throughout course of therapy (phleum (A): 13.22%±2.28, phleum (K): 6.73%±0.66; p<0.01). Regulatory T cells were also allergen-specifically induced, but only in cultures prior treatment (medium (A): 0.84%±0.30, phleum (A): 2.29%±0.55; p<0.05). Similarly, the present inventors observed an even stronger effect in the Tr17 compartment, which was also antigen-specifically induced at baseline (medium (A): 6.74%±1.90, phleum (A): 36.65%±7.24; p<0.0001). However, comparably to Th17 cells, the allergen-driven boost of Tr17 cells faded throughout the course of immunotherapy (phleum (A): 36.65%±7.24, phleum (K): 24.94%±6.16; p=0.18; FIG. 4C). Contrary to assumptions, the proportion of IL-10 producing B cells in total B cells was significantly reduced upon phleum encounter (phleum (E): 1.98%±0.53, phleum (K): 0.46%±0.06; p<0.05; FIG. 4D). Overall numbers of memory B cells did not differ dependent on allergen stimulation, while IL-10$^+$ memory B cells were increased initially following the up-dosing period (phleum (A): 3.17%±1.24, phleum (E): 10.07%±5.98; n.s.; FIG. 4F). Further, the present inventors could show, that B cells from grass pollen-allergic patients up-regulate the tolerance-inducing surface marker PD-L1 (CD274) significantly after seven days of in vitro allergen stimulation and that this induction is maintained throughout the treatment course (medium (A): 1.51%±0.22, phleum (A): 10.37%±0.60; p<0.0001; FIG. 4G). In addition, here, the present inventors report elevated production of total IgG4 following the initial up-dosing period in response to in vitro allergen challenge (phleum (A): 19.09%±1.26, phleum (E): 23.89%±2.88, phleum (K): 17.85%±1.75; E vs. K: p<0.05), which coincides with a decrease of total IgE (phleum (A): 1.48%±0.24, phleum (E): 1.38%±0.19, phleum (K): 1.53%±0.18; FIG. 4H,I). Both effects were abolished after three years of ongoing therapy. Serum levels of grass-pollen specific IgG4 and IgE were analyzed throughout treatment course and showed a significant increase of IgG4 during the first year of therapy (data not shown).

Figure 5:
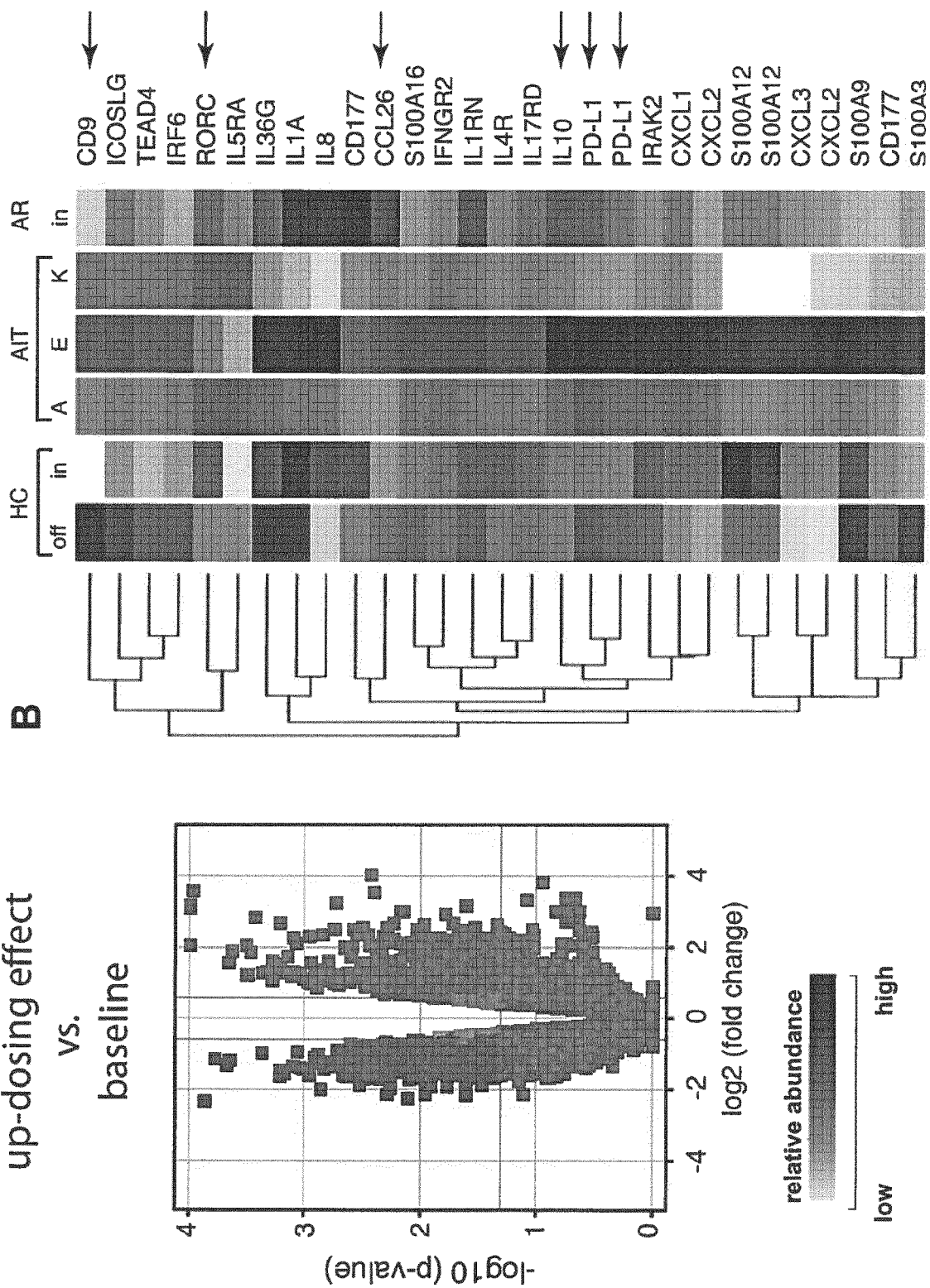
FIG. 5 shows that local gene expression changes indicate shifts in regulatory hierarchies in the nasal mucosa.

Example 6—Local Gene Expression Changes Indicate Shifts in Regulatory Hierarchies in the Nasal Mucosa FIG. 5 shows the following: Nasal scrapings were taken from healthy control subjects during off season (HC off; n=3), in grass pollen season (HC in; n=3), treated patients throughout course of therapy at time points A (Baseline; n=6), E (6 h after last initial top dose injection; n=5), and K (last in season after three years of follow-up; n=9), untreated allergic rhinitis patients in grass pollen season (AR in; n=5) and subjected to RNA whole transcriptome microarray analysis. (A) Volcano plot of statistically significant entities (p<0.05; FC≥1.5) comparing time point E (up-dosing effect) and A (baseline). (B) Comparison of E versus A depicts an extract of significant gene expression changes following initial AIT (p<0.05; FC≥1.5). Selection of entities is shown, which are relevant for allergy. (C) Volcano plot of statistically significant entities (p<0.05; FC≥1.5) comparing time point K (long-term therapy effect in grass pollen season) and untreated allergic patients in grass pollen season (AR in). (D) Comparison of K versus untreated allergic patients in grass pollen season (AR in) mirrors therapeutic effects on significant gene expression changes (p<0.05; FC≥1.5) in nasal transcriptome. Entity selection of interleukins is shown. The color code indicates the abundance of transcripts ranging from low to high.

Global gene expression analysis from nasal scrapings identified several crucial gene expression changes in the up-dosing phase and after long-term treatment. Comparison of the short-term AIT effects (E versus A) unraveled gene expression changes of immune- and epithelial-cell origin that reflects the systemic picture including the key Breg genes MO, PD-L1 (also known as CD274) and previously described CD9 (FIG. 5A,B). The maximal expression of these genes was detected following initial up-dosing treatment (E) with a strong decrease following long-term AIT (K), where IL10 and CD274 fell below levels of untreated allergic patients. CCL26, a well-known IL-4-inducible epithelial marker, follows the systemic Th2 response over time, however on epithelial level in the upper airways. Notably, RORC expression resembles the contrary effect and therefore aligns with the systemic course of Th17 cells throughout AIT.

In addition, long-term treatment effects were characterized by decreased expression levels of multiple cytokines of the Th2 response, IL4, IL5, IL13 and epithelial type 2 (E2) response, IL24 (FIG. 5C,D). Notably, IL17B and IL17C, the latter a pro-inflammatory IL-17 isoform produced by the nasal epithelial cells, and further, the up-regulation of IL10RB, a main part of the IL-10 receptor complex, were significantly reduced upon AIT.

Example 7

(a) Local Shifts of Immune Cell Compartments Following AIT

Figure 6:
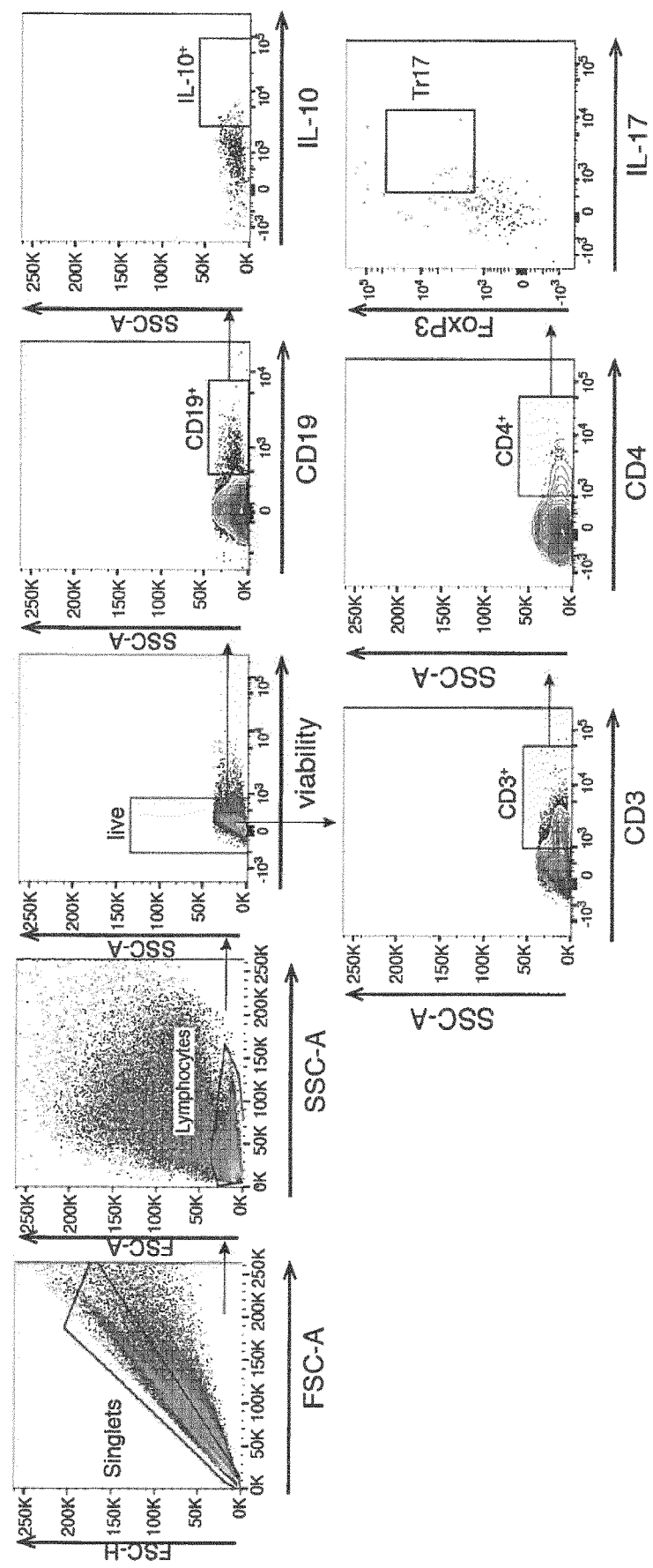
FIG. 6 shows local shifts of immune cell compartments following allergen-specific immunotherapy.

FIG. 6 shows the following: Lymphocytes were extracted from nasal scrapings from healthy control individuals (HC; n=11), allergic rhinitis patients without AIT (AR−AIT; n=8), and allergic rhinitis patients with long-term AIT (AR+AIT; n=11) in grass pollen season, and subjected to intracellular antigen staining. Different immune cell subsets were analyzed using flow cytometry: gating strategy for nasal samples; (A) IL-17$^+$ CD4$^+$ Th17 cells; (B) IL-17$^+$/FoxP3$^+$-co-expressing CD4$^+$ Tr17 cells; (C) FoxP3$^+$ Treg cells; (D) IL-10-producing FoxP3$^+$ Treg cells; (E) total B cells; (F) IL-10$^+$ regulatory B cells. Data are depicted as scatter plots showing all data points and median. Two-sided Mann-Whitney T-tests were used to test for significant differences between sample groups.

(b) Breg/Th17 Ratios at Time Point E Indicate Success of Long-Term AIT

Spearman correlation analysis was performed comparing the Retrospective Assessment of Allergic Symptoms (RAAS) at time point K (last in season after three years of follow-up) with (G) total Breg numbers at time point E (six hours after last initial top dose injection) (n=14) or (H) with the in-/reduction of Bregs of time point E minus A (Baseline) (n=15). (I) Spearman correlation of RAAS at time point K with the ratio of Breg percentage to Th17 percentage at time point E (n=14). One patient was excluded from correlation (I) because it presented as outlier. One patient was excluded from all correlations due to co-sensitization with house dust mite (HDM) after three years of treatment. Statistically significant differences were defined asp values *p<0.05, p<0.01, *p<0.001, ****p<0.0001.

Using intracellular flow cytometry on nasal scrapings, for the first time, the present inventors could show a change in effector and regulatory immune cell subsets in the upper airways of allergic patients. Non-significant trends for nasal decreased Th17 and increased Tr17 populations, reflecting our systemic and local findings, were observed comparing long-term treated patients with untreated allergies in grass pollen season (Th17: untreated: 8.67%±2.28, treated: 7.43%±1.22; n.s./Tr17: untreated: 11.88%±4.13, treated: 12.61%±4.37; n.s.; FIG. 6A,B). FoxP3$^+$ Tregs cells tend to increase upon AIT (untreated: 3.19%±0.88, treated: 5.05%±0.82; n.s.; FIG. 6C), while local IL-10 production by this population showed a robust significant increase (untreated: 1.69%±1.69, treated: 15.54%±6.04; p<0.05; FIG. 6D). Additionally, AIT treated patients showed higher local numbers of total B cells (untreated: 11.38% 3.90, treated: 20.53%±3.45; p=0.06) and regulatory B cells (untreated: 2.82%±1.13, treated: 3.10%±0.61; n.s; FIG. 6E,F).

Finally, total frequencies of regulatory B cells as well as the differential frequencies of Delta(Bregs(A)-Bregs(K)) correlated positively with the Retrospective Assessment of seasonal Allergic Symptoms Score (RAAS) (r=0.58, p=0.032; r=0.52, p=0.047; FIG. 6G,H). Strikingly, the ratio of cell frequencies of regulatory B cells to Th17 effector cells following the initial up-dosing phase correlated strongly with RAAS after three years of AIT with a p-value beyond 0.001 (r=0.82; p=0.0006; FIG. 6I).

CONCLUSION

An early prediction of therapy success would represent a breakthrough for allergen-specific immunotherapy. In the above examples, the present inventors have shown and provided evidence for the first time that a shift in lymphocyte subsets is related and indicative for therapy success. The set of experiments described above confirms that an early response to AIT involves an IL-10 induction in B-cells and T-cells, and shows for the first time restriction of allergen-specific Th17 response, both systemically and in the upper airways. Without wishing to be bound by any theory, the present inventors presume that a mediation of suppression of Th1 and Th17 differentiation occurs by IL-10 secretion by regulatory B-cells, and they assume that this underlies the inverse dynamics of circulating Th17 and Breg cells observed in the above set of experiments. The present inventors link, for the first time, a late tolerance mounting phase in allergen-specific immunotherapy to an initial up-dosing phase, as circulating Breg/Th17 ratios after the initial AIT up-dosing phase correlate strongly with patient self-assessed outcome following therapy conclusion after three years.

The features of the present invention discloses in the specification, the claims, and/or in the accompanying drawings may, both separately and in any combination thereof, be material for realizing the invention in various forms thereof. Further modifications of the preferred embodiments are possible without leaving the scope of the invention which is solely defined by the claims.

The invention claimed is:

1. A method of predicting therapeutic success of an allergen-specific immunotherapy (AIT) in a patient suffering from or having a disposition to develop an allergic disease selected from hay fever, allergic rhinitis, allergic asthma, allergic conjunctivitis, food allergy and stinging insect hypersensitivity, wherein said method comprises the steps:

administering an allergen repeatedly to the patient in increasing doses of said allergen up to a maximum dose effective to induce immunologic tolerance to said allergen in said patient;
administering said allergen to the patient at said maximum dose;
determining a ratio of interleukin-10 producing regulatory B-cells (IL-10$^+$ Bregs) and interleukin-17 producing T-helper cells (Th17) of said patient, said ratio being represented by IL-10$^+$Bregs/Th17, predicting therapeutic success of an allergen-specific immunotherapy in said patient, if said determined ratio exceeds a defined threshold; and
continuing the allergen-specific immunotherapy in said patient at said maximum dose.

2. The method according to claim 1, wherein said allergen-specific immunotherapy involves subcutaneous injection of an allergen and comprises an initial induction phase, where said allergen is repeatedly subcutaneously administered to a patient in increasing doses of said allergen up to a maximum dose effective to induce immunologic tolerance to said allergen in said patient, and a maintenance phase, wherein said allergen is subcutaneously administered repeatedly to said patient at said maximum dose, wherein said maintenance phase comprises a first subphase ("top dose phase") wherein said allergen is subcutaneously administered repeatedly at said maximum dose in a weekly or biweekly interval, and a second subphase ("treatment maintenance phase"), wherein said allergen is subcutaneously administered repeatedly at the same maximum dose in intervals longer than during the top-dose phase,
wherein said ratio is determined 4-10 hours after administration of any maximum dose of said top-dose phase.

3. The method according to claim 1, wherein said allergen-specific immunotherapy involves sublingual administration of an allergen and comprises an initial induction phase, where said allergen is sublingually administered to a patient in increasing doses of said allergen up to a maximum dose effective to induce immunologic tolerance to said allergen in said patient, and a maintenance phase, wherein said allergen is repeatedly sublingually administered to said patient at said maximum dose,
wherein said ratio is determined within the first 1-7 weeks of said maintenance phase.

4. The method according to claim 1, wherein said ratio is determined in one or several samples obtained from said patient, said sample(s) being selected from whole blood, peripheral blood mononuclear cells (PBMCs), nasal cells obtained from nasal scrapings or a nasal biopsy of said patient, bronchial cells obtained from sputum, a lung biopsy or bronchial alveolar lavage fluid (BALF) of said patient.

5. The method according to claim 1, wherein therapeutic success is measured by a patient-assessed retrospective assessment of seasonal allergic symptoms (RAAS), or by combined symptom medication score (CSMS) or by visual analog scale (VAS).

6. The method according to claim 1, wherein said ratio IL-10$^+$ Bregs/Th17 is a ratio of gene expression signatures of IL-10$^+$ Bregs versus gene expression signatures of Th17 and is determined by determining gene expression signatures of IL-10$^+$ Bregs versus gene expression signatures of Th17 cells.

7. The method according to claim 1, wherein said ratio of interleukin-10 producing regulatory B-cells (IL-10$^+$ Bregs) and interleukin-17 producing T-helper cells (Th17), represented by IL-10$^+$ Bregs/Th17, is a ratio of cell counts of these cells.

8. The method according to claim 7, wherein said step of predicting comprises predicting therapeutic success of an allergen-specific immunotherapy in said patient, if said determined ratio of cell counts has a value in the range of $\geq 1.2$, or comprises predicting no therapeutic success if said determined ratio of cell counts has a value in the range $<1.2$.

9. The method according to claim 7, wherein said method of predicting therapeutic success comprises determining said ratio of cell counts, IL-10$^+$ Bregs/Th17, and said ratio of cell counts is determined by determining relative cell counts for both IL-10$^+$ Bregs and Th17 cells and by subsequently calculating the ratio of these relative cell counts, wherein said relative cell count of IL-10$^+$ Bregs cells is determined as number of IL-10 Bregs with reference to the number of live CD19$^+$ B-cells, and wherein said relative cell count of Th17 cells is determined as number of Th17 cells with reference to the number of live CD4$^+$ CD3$^+$ T-cells.

10. The method according to claim 9, wherein said cell counts of IL-10$^+$ Bregs and of Th17 cells are determined by a method selected from flow cytometry, fluorescence-activated cell sorting (FACS), determining cell counts by means of a Coulter counter, haemocytometer, image analysis or spectrophotometry.

11. The method according to claim 1, wherein said method of predicting therapeutic success of an allergen-specific immunotherapy is an in-vitro method.

12. The method according to claim 1, wherein said allergic disease is selected from allergic rhinitis, hay fever and allergic asthma, and wherein said allergen is selected from pollen fungi, fungal spores, dust, mites, and animal dander.

13. The method, according to claim 2, wherein said ratio is determined 3-9 hours after administration of the last maximum dose of said top-dose phase.

14. The method, according to claim 3, wherein said ratio is determined 3-9 hours after administration of any maximum dose of said maintenance phase within said first 1-7 weeks of said maintenance phase.

15. The method, according to claim 6, wherein gene expression signatures are determined by a method selected from transcriptome-based assays, real time PCR and protein detection methods.

* * * * *

UNITED STATES PATENT AND TRADEMARK OFFICE
CERTIFICATE OF CORRECTION

PATENT NO. : 11,821,894 B2
APPLICATION NO. : 16/625503
DATED : November 21, 2023
INVENTOR(S) : Carsten B. Schmidt-Weber et al.

It is certified that error appears in the above-identified patent and that said Letters Patent is hereby corrected as shown below:

In the Specification

Column 9,
Line 60, "in in/from" should read --in--

Column 11,
Line 16, "IL-10 Bregs" should read --IL-10$^+$ Bregs--
Line 19, "CD4 CD3 T-cells" should read --CD4$^+$ CD3$^+$ T-cells--
Line 49, "Patent characteristics" should read --Patient characteristics--

Column 12,
Line 32, "452-461)" should read --452-461).--

Column 14,
Line 27, "asp values" should read --as p values--

Column 15,
Line 27, "asp values" should read --as p values--
Line 63, "CD4 Th2" should read --CD4$^+$ Th2--

Column 16,
Line 28, "a significantly level" should read --a significant level--
Line 41, "CD1dCD5$^+$" should read --CD1d$^+$ CD5$^+$--

Column 17,
Line 41, "asp values" should read --as p values--

Column 19,
Line 66, "asp values" should read --as p values--

Signed and Sealed this
Twenty-sixth Day of March, 2024

Katherine Kelly Vidal
*Director of the United States Patent and Trademark Office*

Column 20,
Line 17, "11.38% 3.90," should read --11.38% ± 3.90,--

In the Claims

Column 22,
Line 27, "IL-10 Bregs" should read --IL-10$^+$ Bregs--
Line 46, "3-9 hours" should read --4-10 hours--
Line 49, "3-9 hours" should read --4-10 hours--